(12) United States Patent
Berge et al.

(10) Patent No.: US 6,943,175 B2
(45) Date of Patent: Sep. 13, 2005

(54) 2-NH-HETEROARYLIMIDAZOLES WITH ANTIBACTERIAL ACTIVITY

(75) Inventors: John Berge, Harlow (GB); Andrew Forrest, Harlow (GB); Dieter Hamprecht, Verona (IT); Richard Jarvest, Stevenage (GB)

(73) Assignee: Replidyne, Inc., Louisville, CO (US)

( * ) Notice: Subject to any disclaimer, the term of this patent is extended or adjusted under 35 U.S.C. 154(b) by 0 days.

(21) Appl. No.: 10/729,416

(22) Filed: Dec. 5, 2003

(65) Prior Publication Data

US 2004/0147548 A1 Jul. 29, 2004

(30) Foreign Application Priority Data

Dec. 6, 2002 (GB) .............................................. 0228545

(51) Int. Cl.[7] ...................... A61K 31/437; C07D 471/04
(52) U.S. Cl. ........................ 514/303; 546/118; 544/236; 544/264; 544/350; 548/303.7; 514/248; 514/249; 514/261; 514/393
(58) Field of Search ................................. 514/303, 248, 514/249, 261, 393; 546/118; 544/236, 264, 350; 548/303.7

(56) References Cited

FOREIGN PATENT DOCUMENTS

| EP | 0 785 268 | 7/1997 |
|---|---|---|
| WO | WO 00/71522 | * 11/2000 ......... C07D/235/30 |

OTHER PUBLICATIONS

Van der Wenden et al. (1995) European J. Pharma. 290:189–199.

Peyman et al. (2000) Angew. Chem. Int. Ed. 39(16):2874–2877.

Jarvest et al. (2002) J. Med. Chem. 45(10):1959–1962.

Iwao et al. (1992) Heterocycles 34(5):1031–1038.

Barlin et al. (1982) Aust. J. Chem. 35:2299–2306.

Fleischmann et al. (1995) Science 269:496–519.

Lespagnol et al. (1968) Ann. Pharm. Fr. 26(3):207–214 (and abstract in English).

* cited by examiner

Primary Examiner—Charanjit S. Aulakh
(74) Attorney, Agent, or Firm—Swanson & Bratschun LLC

(57) ABSTRACT

Compounds of formula (I):

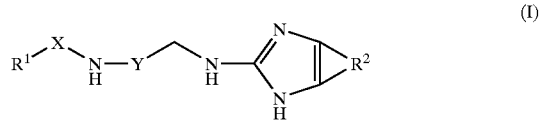

are inhibitors of bacterial methionyl tRNA synthetase and are of use in treating bacterial infections.

7 Claims, No Drawings

2-NH-HETEROARYLIMIDAZOLES WITH ANTIBACTERIAL ACTIVITY

CROSS-REFERENCE TO RELATED APPLICATIONS

This application claims the benefit under 35 U.S.C. § 119(b)(1) of United Kingdom patent application serial number 0228545.0, filed Dec. 6, 2002.

FIELDS OF THE INVENTION

The present invention relates to novel 2-NH-heteroarylimidazoles which are inhibitors of bacterial methionyl t-RNA synthetase (MRS), processes for their preparation and their use in therapy as anti-bacterial agents.

BACKGROUND OF THE INVENTION t-RNA synthetases are involved in protein biosynthesis so that inhibition thereof may be expected to lead to a cessation of cell growth. Thus, for instance, the compound mupirocin, produced by the organism *Pseudomonas fluorescens*, is an anti-bacterial agent and is used as the active ingredient in the product Bactroban, marketed by GlaxoSmithKline. Mupirocin has been shown to be an inhibitor of the isoleucyl t-RNA synthetase. Each t-RNA synthetase represents a separate target for drug discovery. t-RNA synthetase inhibitors which are selective for bacterial cells over mammalian cells are of considerable therapeutic interest as they have the potential to be used as anti-bacterial agents.

The sequence of the t-RNA synthetase genes in the Gram positive organism *S aureus* have recently been determined (see, for instance, European Patent application no 97300317.1, SmithKline Beecham, for *S aureus* MRS), thereby assisting the process of identifying inhibitors. In addition, the sequence of t-RNA synthetase genes in other pathogenic bacteria, for instance the Gram negative organism *H influenzae*, has also been published (R. D. Fleischmann et al., Science, 269, 496–512, 1995).

Lespagnol et al have described a group of 8-substituted theophylline derivatives, in particular 8-[2-(benzylamino)ethylamino]theophylline, which have hypotensive activity (Ann Pharm Fr, 1968, 26(3), 207–14).

DETAILED DESCRIPTION OF THE INVENTION

We have now found a novel class of 2-NH-substituted heteroarylimidazoles which are potent inhibitors of bacterial methionyl t-RNA synthetase. Accordingly, the present invention provides a compound of the formula (I):

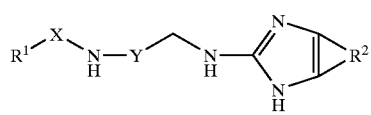

(I)

in which:

$R^1$ is an optionally substituted aryl or an optionally substituted heteroaryl ring;

$R^2$ is the residue of a 5 or 6-membered heteroaryl ring which is optionally substituted with from 1 to 3 substituents selected from halo, cyano, hydroxy, ($C_{1-6}$)alkyl (optionally substituted by halo, hydroxy, amino, mono to perfluoro($C_{1-3}$)alkyl, carboxy or ($C_{1-6}$)alkoxycarbonyl), ($C_{3-7}$)cycloalkyl, $C_{(1-6)}$alkoxy, amino, mono- or di-($C_{1-6}$)alkylamino, acylamino, carboxy, ($C_{1-6}$)alkoxycarbonyl, carboxy($C_{1-6}$)alkyloxy, ($C_{1-6}$)alkylthio, ($C_{1-6}$)alkylsulphinyl, ($C_{1-6}$)alkylsulphonyl, sulphamoyl, mono- and di-($C_{1-6}$)alkylsulphamoyl, carbamoyl, mono- and di-($C_{1-6}$)alkylcarbamoyl, and heterocyclyl;

X is $CH_2$ or $CHR^3$ in which $R^3$ is $C_{(1-6)}$alkyl or is linked to the ortho position of an aryl or heteroaryl ring of $R^1$ to form a 5 to 7 membered ring optionally including oxygen or nitrogen as a ring atom;

Y is $C_{(1-3)}$alkylene or $C_{(4-6)}$cycloalkylene;

including tautomeric forms of the imidazole ring; and salts thereof, preferably pharmaceutically acceptable salts thereof, and excluding 8-[2-(benzylamino)ethylamino]theophylline.

Compounds of formula (I) are inhibitors of bacterial methionyl tRNA synthetase.

Representative examples of $R^1$ when aryl include phenyl and naphthyl, preferably phenyl, each of which may be optionally substituted with up to three substituents. Representative examples of such substituents include $C_{(1-6)}$ alkyl, $C_{(1-6)}$ alkenyl, $C_{(1-6)}$ alkynyl, $C_{(1-6)}$ alkoxy, halo, cyano, amino, sulphamoyl, phenylcarbonyl, aryl, and benzyloxy. Preferably, the phenyl or naphthyl is substituted by two or three substituents such as halo, $C_{(1-6)}$ alkyl, $C_{(1-6)}$ alkenyl, $C_{(1-6)}$ alkynyl, $C_{(1-6)}$ alkoxy or $C_{(1-6)}$ alkylthio.

Representative examples of $R^1$ when heteroaryl include pyrrolyl, thienyl, furanyl, pyridyl, quinolinyl, benzofuranyl, and indolyl, preferably thienyl or indolyl, each of which may be optionally substituted with up to three substituents. Preferably, the heteroaryl ring is substituted by two or substituents such as halo, optionally substituted $C_{(1-6)}$ alkyl, optionally substituted $C_{(1-6)}$ alkenyl, $C_{(1-6)}$ alkynyl, or $C_{(1-6)}$ alkoxy. Representative examples of such substituents include halo, mono to perfluoro$C_{(1-6)}$alkyl and mono to perfluoro$C_{(1-6)}$alkenyl.

Preferred examples of aryl and heteroaryl groups for $R^1$ include phenyl, indolyl and thienyl.

Representative heteroaryl rings formed by $R^2$ are nitrogen-containing heteroaryl rings, having 6 ring atoms and including one or two nitrogen atoms, for instance b- or c-pyrido, d-pyridimo or c-pyridazino; or sulfur-containing heteroaryl rings, having 5 ring atoms, for instance c-thieno. Preferably, the heteroaryl ring is unsubstituted. Preferably, the ring is c-pyridazino.

Representative examples of X include $CH_2$ or forming with $R^1$ a 5–7-membered ring fused to an aryl or heteroaryl ring, preferably including oxygen or nitrogen as a ring atom, for instance tetrahydroquinolinyl and chromanyl.

Representative examples of Y include a $C_2$ alkylene chain or a 1,2-cyclopentylene group.

Salts may be formed from inorganic and organic acids. Representative examples of suitable inorganic and organic acids from which pharmaceutically acceptable salts of compounds of formula (I) may be formed include maleic, fumaric, benzoic, ascorbic, pamoic, succinic, bismethylenesalicylic, methanesulfonic, ethanedisulfonic, acetic, propionic, tartaric, salicylic, citric, gluconic, aspartic, stearic, palmitic, itaconic, glycolic, p-aminobenzoic, glutamic, benzenesulfonic, hydrochloric, hydrobromic, sulfuric, cyclohexylsulfamic, phosphoric and nitric acids.

When used herein, the term "alkyl" and similar terms such as "alkoxy" includes all straight chain and branched isomers. Representative examples thereof include methyl, ethyl, n-propyl, iso-propyl, n-butyl, sec-butyl, iso-butyl, t-butyl, n-pentyl and n-hexyl.

When used herein, the terms "alkenyl" and "alkynyl" include all straight chain and branched isomers. Representative examples thereof include vinyl, ethynyl and 1-propynyl.

Preferred substituents for alkyl and alkenyl groups include, for example, and unless otherwise defined, halogen, cyano, azido, nitro, carboxy, $(C_{1-6})$alkoxycarbonyl, carbamoyl, mono- or di-$(C_{1-6})$alkylcarbamoyl, sulpho, sulphamoyl, mono- or di-$(C_{1-6})$alkylsulphamoyl, amino, mono- or di-$(C_{1-6})$alkylamino, acylamino, ureido, $(C_{1-6})$ alkoxycarbonylamino, 2,2,2-trichloroethoxycarbonylamino, aryl, heterocyclyl, hydroxy, $(C_{1-6})$alkoxy, acyloxy, oxo, acyl, 2-thienoyl, $(C_{1-6})$alkylthio, $(C_{1-6})$alkylsulphinyl, $(C_{1-6})$alkylsulphonyl, hydroxyimino, $(C_{1-6})$alkoxyimino, hydrazino, hydrazono, benzohydroximoyl, guanidino, amidino and iminoalkyl amino.

When used herein, the term "aryl" includes, unless otherwise defined, phenyl or naphthyl optionally substituted with up to five, preferably up to three substituents.

When substituted, an aryl group may have up to three substituents. Preferred substituents for an aryl group include, for example, and unless otherwise defined, halogen, cyano, $(C_{1-6})$alkyl, mono to perfluoro$(C_{1-3})$alkyl, $(C_{3-7})$cycloalkyl, $(C_{2-6})$alkenyl, $(C_{1-6})$alkoxy, $(C_{2-6})$alkenoxy, aryl$C_{(1-6)}$ alkoxy, halo$(C_{1-6})$alkyl, hydroxy, amino, mono- or di-$(C_{1-6})$alkylamino, acylamino, nitro, carboxy, $(C_{1-6})$ alkoxycarbonyl, $(C_{1-6})$alkenyloxycarbonyl, $(C_{1-6})$ alkoxycarbonyl$(C_{1-6})$alkyl, carboxy$(C_{1-6})$alkyl, $(C_{1-6})$ alkylcarbonyloxy, carboxy$(C_{1-6})$alkyloxy, $(C_{1-6})$ alkoxycarbonyl$(C_{1-6})$alkoxy, $(C_{1-6})$alkylthio, $(C_{1-6})$ alkylsulphinyl, $(C_{1-6})$alkylsulphonyl, sulphamoyl, mono- and di-$(C_{1-6})$-alkylsulphamoyl, carbamoyl, mono- and di-$(C_{1-6})$alkylcarbamoyl, and heterocyclyl.

When used herein, the term "heteroaryl" includes single or fused rings comprising up to four hetero-atoms in the ring selected from oxygen, nitrogen and sulphur. Preferably the heteroaryl ring comprises from 4 to 7, preferably 5 to 6, ring atoms. A fused heteroaryl ring system may include carbocyclic rings and need only include one heterocyclic ring.

When used herein, the term "heterocyclyl" includes aromatic and non-aromatic single or fused rings comprising up to four hetero-atoms in the ring selected from oxygen, nitrogen and sulphur. Suitably the heterocyclic ring comprises from 4 to 7, preferably 5 to 6, ring atoms. A fused heterocyclic ring system may include carbocyclic rings and need only include one heterocyclic ring.

When substituted, a heteroaryl or a heterocyclyl group may have up to three substituents. Preferred such substituents include those previously mentioned for an aryl group as well as oxo.

When used herein, the terms "halogen" and "halo" include fluorine, chlorine, bromine and iodine and fluoro, chloro, bromo and iodo, respectively.

The compounds according to the invention are suitably provided in substantially pure form, for example at least 50% pure, suitably at least 60% pure, advantageously at least 75% pure, preferably at least 85% pure, more preferably at least 95% pure, especially at least 98% pure, all percentages being calculated as weight/weight. An impure or less pure form of a compound according to the invention may, for example, be used in the preparation of a more pure form of the same compound or of a related compound (for example a corresponding derivative) suitable for pharmaceutical use.

It will be appreciated that certain compounds of the present invention may comprise one or more chiral centres so that compounds may exist as stereoisomers, including diastereoisomers and enantiomers. The present invention covers all such stereoisomers, and mixtures thereof, including racemates.

Preferred compounds of formula (I) include the compounds of Examples 2, 3, 6, 9, 11, 12, 15, 17, 22, 30, 32, 34–37, 39–41, and 43–44.

A compound of formula (I) may be prepared by reacting an imidazole compound of formula (II):

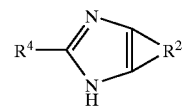

(II)

in which $R^2$ is as hereinbefore defined; and
$R^4$ is a leaving group such as halo, for instance chloro, or $C_{(1-6)}$ alkylthio;
with an amine of the formula (III):

$$R^1XNHYCH_2NH_2 \quad \text{(III)}$$

in which $R^1$, X and Y are as hereinbefore defined;
or an activated derivative thereof;
under nucleophilic displacement conditions.

Suitable conditions are well known in the art and include the use of a large excess of the compound of formula (III) to drive the reaction to completion and heating at a temperature of 60–130° C. Addition of a base may be advantageous in some cases, eg a tertiary base such as N,N-di(cyclohexyl)ethylamine.

A compound of formula (I) may also be prepared by reacting a compound of formula (IV):

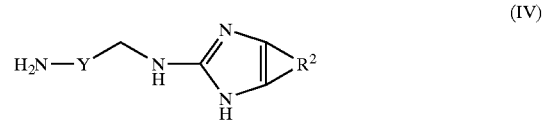

(IV)

in which $R^2$ and Y are as hereinbefore defined;
with either:
 (a) for a compound of formula (I) in which X is $CH_2$, an aldehyde of formula (V):

$$R^1CHO \quad \text{(V)}$$

in which $R^1$ is as hereinbefore defined;
under reductive alkylation conditions; or
 (b) for a compound of formula (I) in which X is $CHR^3$, a ketone of formula (VI):

$$R^1R^3CO \quad \text{(VI)}$$

in which $R^1$ and $R^3$ are as hereinbefore defined;
under reductive alkylation conditions.

Suitable reductive alkylating conditions are well known in the art and include for instance, the use of sodium triacetoxyborohydride in a solvent system such as DMF/acetic acid or sodium cyanoborohydride in methanol/acetic acid. Reductive alkylation with an aldehyde is typically carried out at room temperature for a period of 1–16 h. Reductive alkylation with a ketone is typically carried out in refluxing methanol for a period of 16–40 h.

A compound of formula (IV) may be prepared by reacting a compound of formula (II) with a compound of formula (III) in which $R^1X$ is hydrogen.

Alternatively, compounds of formula (I) in which Y is $C_{(1-3)}$alkylene may be prepared by a reductive amination process in which the amine and aldehyde/ketone are reversed. Thus, in a further aspect, the present invention provides for a process for preparing a compound of formula (I) in which Y is $C_{(1-3)}$alkylene which process comprises reacting a compound of formula (VII):

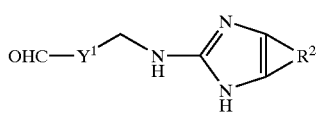

in which $R^2$ is as hereinbefore defined, and
$Y^1$ is $C_{(0-2)}$alkylene;
with an amine of formula (VIII):

in which $R^1$ and X are as hereinbefore defined;
under reductive alkylation conditions, as hereinbefore described.

A compound of formula (VII) may be prepared in a similar way to a compound of formula (IV), using a compound of formula (II) and an amine of the formula $(C_{(1-6)}$alkoxyl$)_2$CHY$^1$CH$_2$NH$_2$, followed by acid hydrolysis to liberate the aldehyde from the acetal.

Compounds of formula (VIII) are amines and are either commercially available or may be prepared form available starting materials using methods well known in the art for preparing amines, for instance by functional group interconversion.

The compounds of this invention are active against a range of important pathogenic bacteria, including Gram positive organisms, such as Staphylococci, for instance S. aureus Oxford and coagulase negative strains of Staphylococci such as S. epidermidis; Streptococci, for instance S. pyogenes CN10 and S. pneumoniae R6; and Enterococci, for instance Ent. faecelis I. Preferably, compounds of this invention are also active against Gram negative organisms, such as Haemophilus, for instance H. influenzae Q1; Moraxella, for instance M. catarrhalis 1502; and Escherichia, for instance E. Coli DC0. The most preferred compounds of the present invention will be active against the organisms S. aureus; S. pneumoniae; Ent. faecelis; H. influenzae and M. catarrhalis.

In addition, compounds of this invention are active against Staphylococci organisms such as S. aureus and coagulase negative strains of Staphylocci such as S. epidermidis which are resistant (including multiply-resistant) to other anti-bacterial agents, for instance, β-lactam antibiotics such as, for example, methicillin; macrolides; aminoglycosides, and lincosamides. Compounds of the present invention are therefore useful in the treatment of MRSA and MRCNS.

Compounds of the present invention are also active against strains of E. faecalis including vancomycin resistant strains and therefore of use in treating infections associated with VRE organisms. Furthermore, compounds of the present invention are useful in the treatment of Staphylococci organisms which are resistant to mupirocin.

Bacterial infections which may be treated include respiratory tract infections, otitis media, meningitis, endocarditis, skin and soft tissue infections in man, mastitis in cattle, and also respiratory infections in farm animals such as pigs and cattle. Accordingly, in a further aspect, the present invention provides a method of treating bacterial infection in human or non-human animals, which method comprises administering a therapeutically effective amount of a compound of formula (I) as hereinbefore defined, to a human or non-human animal in need of such therapy. It will be appreciated that a compound of the present invention which has a broad spectrum of anti-bacterial activity, including activity against both Gram positive and Gram negative bacteria will be of general use in the community for the empiric treatment of community acquired infections. In comparison, a compound of the present invention with a more limited spectrum, for instance activity against Gram positive bacteria, is more likely to be used in circumstances where the causative pathogenic organism has been identified.

The present invention provides a pharmaceutical composition comprising a compound of formula (I) together with a pharmaceutically acceptable carrier or excipient.

The present invention also provides a method of treating bacterial infections in animals, especially in humans and in domesticated mammals, which comprises administering a compound of formula (I), or a composition according to the invention, to a patient in need thereof.

The invention further provides the use of a compound of formula (I) in the preparation of a medicament composition for use in the treatment of bacterial infections.

The compounds and compositions according to the invention may be formulated for administration in any convenient way for use in human or veterinary medicine, by analogy with other antibiotics.

The compounds and compositions according to the invention may be formulated for administration by any route, for example oral, topical or parenteral. The compositions may, for example, be made up in the form of tablets, capsules, powders, granules, lozenges, creams, syrups, or liquid preparations, for example solutions or suspensions, which may be formulated for oral use or in sterile form for parenteral administration by injection or infusion.

Tablets and capsules for oral administration may be in unit dosage form, and may contain conventional excipients including, for example, binding agents, for example, syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; and pharmaceutically acceptable wetting agents, for example sodium lauryl sulphate. The tablets may be coated according to methods well known in normal pharmaceutical practice.

Oral liquid preparations may be in the form of, for example, aqueous or oily suspensions, solutions, emulsions, syrups or elixirs, or may be presented as a dry product for reconstitution with water or another suitable vehicle before use. Such liquid preparations may contain conventional additives, including, for example, suspending agents, for example sorbitol, methyl cellulose, glucose syrup, gelatin, hydroxyethyl cellulose, carboxymethyl cellulose, aluminium stearate gel or hydrogenated edible fats; emulsifying agents, for example lecithin, sorbitan monooleate or acacia; non-aqueous vehicles (which may include edible oils), for example almond oil, oily esters (for example glycerine), propylene glycol, or ethyl alcohol; preservatives, for example methyl or propyl p-hydroxybenzoate or sorbic acid; and, if desired, conventional flavouring and colour agents.

Compositions according to the invention intended for topical administration may, for example, be in the form of ointments, creams, lotions, eye ointments, eye drops, ear drops, impregnated dressings, and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

Compositions according to the invention may be formulated as suppositories, which may contain conventional suppository bases, for example cocoa-butter or other glycerides.

Compositions according to the invention intended for parenteral administration may conveniently be in fluid unit dosage forms, which may be prepared utilizing the compound and a sterile vehicle, water being preferred. The compound, depending on the vehicle and concentration used, may be either suspended or dissolved in the vehicle. In preparing solutions, the compound may be dissolved in water for injection and filter-sterilised before being filled into a suitable vial or ampoule, which is then sealed. Advantageously, conventional additives including, for example, local anaesthetics, preservatives, and buffering agents can be dissolved in the vehicle. In order to enhance the stability of the solution, the composition may be frozen after being filled into the vial, and the water removed under vacuum; the resulting dry lyophilized powder may then be sealed in the vial and a accompanying vial of water for injection may be supplied to reconstitute the liquid prior to use. Parenteral suspensions may be prepared in substantially the same manner except that the compound is suspended in the vehicle instead of being dissolved and sterilisation cannot be accomplished by filtration. The compound may instead be sterilised by exposure to ethylene oxide before being suspended in the sterile vehicle. Advantageously, a surfactant or wetting agent is included in such suspensions in order to facilitate uniform distribution of the compound.

A compound or composition according to the invention may suitably be administered to the patient in an antibacterially effective amount.

A composition according to the invention may suitably contain from 0.1% by weight, preferably from 10 to 60% by weight, of a compound according to the invention (based on the total weight of the composition), depending on the method of administration.

The compounds according to the invention may suitably be administered to the patient at a daily dosage of from 1.0 to 100 mg/kg of body weight. For an adult human (of approximately 70 kg body weight), from 50 to 3000 mg, for example about 1500 mg, of a compound according to the invention may be administered daily. Suitably, the dosage for adult humans is from 5 to 20 mg/kg per day. Higher or lower dosages may, however, be used in accordance with normal clinical practice.

When the compositions according to the invention are presented in unit dosage form, each unit dose may suitably comprise from 25 to 1000 mg, preferable from 50 to 500 mg, of a compound according to the invention.

The following Examples illustrate the present invention.

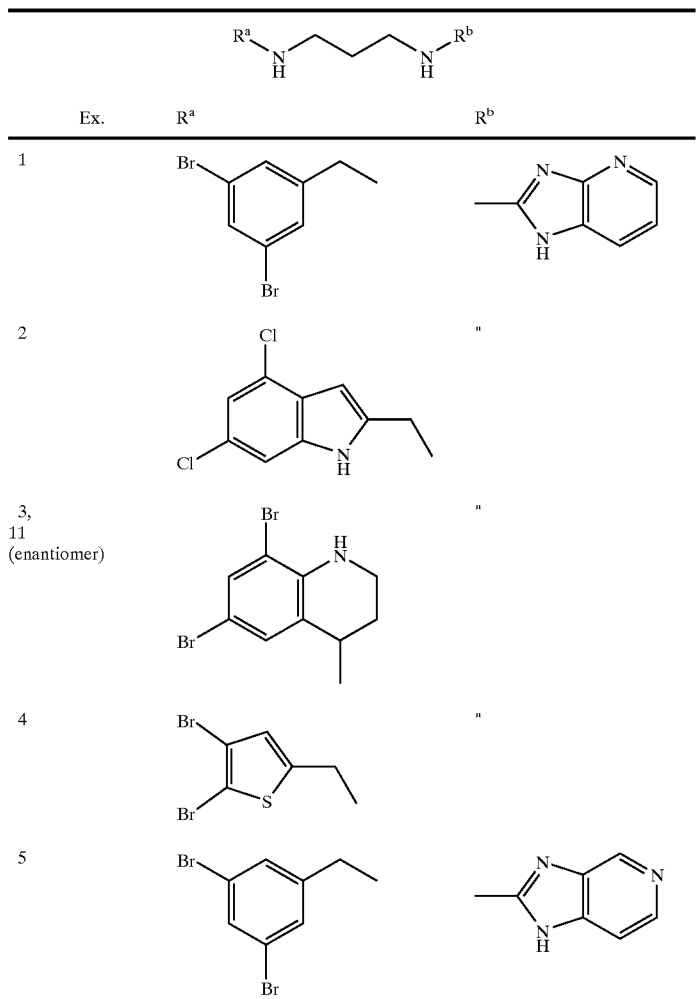

-continued
| Ex. | R$^a$ | R$^b$ |
|---|---|---|
| 6 | 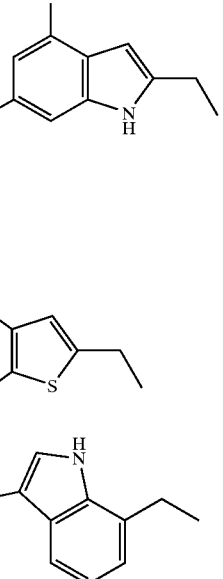 | 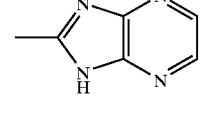 |
| 7 | " | 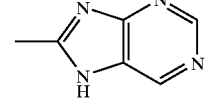 |
| 8 | 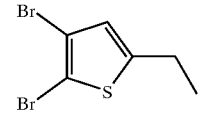 | " |
| 9 | 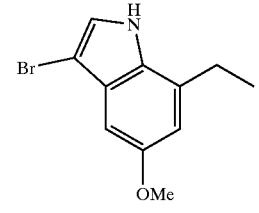 | 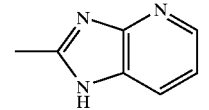 |
| 10 | 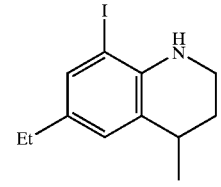 | " |
| 12 | 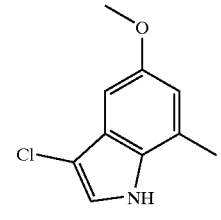 | " |
| 13 | 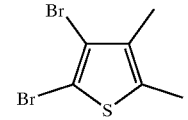 | 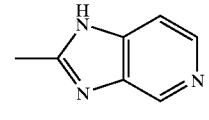 |
| 14 | 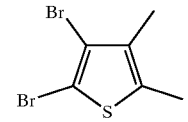 2 HCl | 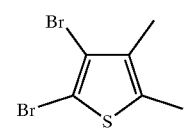 |
| 15 | 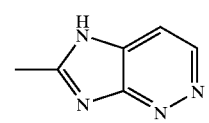 | |

-continued $$R^a\text{-NH-CH}_2\text{CH}_2\text{CH}_2\text{-NH-}R^b$$

| Ex. | R$^a$ | R$^b$ |
|---|---|---|
| 16 | 3-bromo-4,5-dimethyl-2-vinylthiophene | 2-methyl-1H-imidazo[4,5-c]pyridazine |
| 17 | 3-bromo-4,5-dimethyl-2-vinylthiophene | 2-methyl-1H-imidazo[4,5-b]pyridine |
| 18 | 3-bromo-4,5-dimethyl-2-vinylthiophene | 2-methyl-3H-imidazo[4,5-c]pyridine |
| 19 | 3-bromo-2-ethoxy-1-ethyl-5-(methylthio)benzene | 2-methyl-1H-imidazo[4,5-c]pyridazine |
| 20 | 6-chloro-8-iodo-chroman | " |
| 21 | 3-chloro-5-methoxy-7-methyl-1H-indole · 2 HCl | " |
| 22 | 2,3-dibromo-4,5-dimethylthiophene | 2-methyl-1H-imidazo[4,5-c]thiophene |
| 23 | 3-bromo-4,5-dimethyl-2-vinylthiophene | " |

-continued $$\underset{H}{R^a-N}\diagdown\diagdown\underset{H}{N-R^b}$$

| Ex. | Rᵃ | Rᵇ |
|---|---|---|
| 24 | 3-chloro-5-methoxy-7-methyl-1H-indole | " |
| 25 | 3-bromo-5-(difluoromethyl)-2,4-dimethylthiophene · 2 HCl | 2-methyl-1H-imidazo[4,5-b]pyridine |
| 26 | 3-bromo-5-(difluoromethyl)-2,4-dimethylthiophene · 2 HCl | 2-methyl-1H-imidazo[4,5-c]pyridazine |
| 27 | 3-bromo-5-(difluoromethyl)-2,4-dimethylthiophene · 2 HCl | 2-methyl-1H-thieno[3,4-d]imidazole |
| 28 | 3-bromo-2,4-dimethyl-5-(trifluoromethyl)thiophene · 2 HCl | 2-methyl-1H-imidazo[4,5-c]pyridazine |
| 29 | 3-bromo-2,4-dimethyl-5-(trifluoromethyl)thiophene · 2 HCl | 2-methyl-1H-thieno[3,4-d]imidazole |
| 30 | 3-bromo-2,4-dimethyl-5-(trifluoromethyl)thiophene · 2 HCl | 2-methyl-1H-imidazo[4,5-b]pyridine |
| 31 | 3-bromo-2,4-dimethyl-5-(trifluoromethyl)thiophene · 2 HCl | 2-methyl-3H-imidazo[4,5-c]pyridine |
| 32 | 3-bromo-5-(1-fluorovinyl)-2,4-dimethylthiophene · 2 HCl | 2-methyl-1H-imidazo[4,5-b]pyridine |

-continued

| Ex. | Rᵃ | Rᵇ |
|---|---|---|
| 33 | 3-bromo-2-(1-fluorovinyl)-4,5-dimethylthiophene | 2-methyl-1H-imidazo[4,5-c]pyridine |
| 34 | 3-bromo-2-(1-fluorovinyl)-4,5-dimethylthiophene | 2-methyl-1H-imidazo[4,5-c]pyridazine |
| 35 | 3-bromo-2-(1-fluorovinyl)-4,5-dimethylthiophene | 2-methyl-1H-thieno[3,4-d]imidazole |
| 36 | 3-bromo-2-ethynyl-4,5-dimethylthiophene | 2-methyl-1H-imidazo[4,5-c]pyridazine |
| 37 | 3-bromo-2-ethynyl-4,5-dimethylthiophene | 2-methyl-3H-imidazo[4,5-b]pyridine |
| 38 | 3-bromo-2-ethynyl-4,5-dimethylthiophene | 2-methyl-1H-imidazo[4,5-c]pyridine |
| 39 | 3-bromo-2-ethynyl-4,5-dimethylthiophene | 2-methyl-1H-thieno[3,4-d]imidazole |
| 40 | 4-bromo-5-ethyl-2-methyl-3-(propynyl)thiophene · 2 HCl | 2-methyl-1H-imidazo[4,5-c]pyridazine |
| 41 | 4-bromo-5-ethyl-2-methyl-3-(propynyl)thiophene | 2-methyl-3H-imidazo[4,5-c]pyridine |

-continued

| Ex. | Rᵃ | Rᵇ |
|---|---|---|
| 42 | 4-Br, 2-ethyl, 5-methyl, 3-ethynyl-thiophene | 2-methyl-imidazo[4,5-c]pyridine |
| 43 | 4-Br, 2-ethyl, 5-methyl, 3-ethynyl-thiophene | 2-methyl-imidazo[4,5-c]thiophene |
| 44 | 4-Br, 2-cyclopropyl, 5-methyl, 3-methyl-thiophene | 2-methyl-imidazo[4,5-b]pyridazine |

(Parent structure: Rᵃ-NH-CH₂CH₂CH₂-NH-Rᵇ)

General method for reductive amination To a suspension of the amine (0.2 mmol) (containing 0.5 mmol sodium acetate if the amine was present as the dihydrochloride) in methanol (2 ml) was added the aldehyde (0.2 mmol) in methanol (2 ml) and acetic acid (0.033 ml). After stirring under argon for 10 min, NaCNBH$_3$ (24 mg, 0.4 mmol) in MeOH (1 ml) was added and the reaction stirred for 16 h. The reaction mixture was applied to a 2 g Varian Bond Elute SCX cartridge which was flushed with MeOH (8 ml). The cartridge was then eluted with 8 ml 0.2 M NH$_3$ in MeOH, and this eluate evaporated to dryness. The residue was purified by chromatography on silica gel eluting with 2–10% (9:1 MeOH/20 M NH$_3$)in CH$_2$Cl$_2$. Product-containing fractions were combined and evaporated under reduce pressure to give the product as a white solid. To convert this into the corresponding dihydrochloride, the solid was dissolved in 1.0 M HCl in methanol (0.4 ml) and the solution evaporated to dryness.

EXAMPLE 1

N-(3,5-Dibromobenzyl)-N'-(1H-imidazo[4,5-b]pyridin-2-yl)-propane-1,3-diamine a) 1,3-Dihydroimidazo[4,5-b]pyridine-2-thione To 2,3-diaminopyridine (4.36 g, 40 mmol) in pyridine (40 ml) was added carbon disulfide (3.6 ml, 60 mmol). The mixture was heated to 50° C. for 6 h then concentrated to low volume by evaporation under reduced pressure and the residue triturated with tetrahydrofuran. The pale brown solid was collected by filtration and dried to give a first crop of 3.6 g. A second crop (2.44 g) was obtained from the filtrate by re-evaporation and trituration with tetrahydrofuran. m/z (ESI+) 152 (MH⁺, 100%).

b) 2-Methanesulfanyl-1H-imidazo[4,5-b]pyridine To compound 1a (5.55 g, 36.75 mmol) in dry tetrahydrofuran (100 ml) under argon was added triethylamine (5.66 ml, 40 mmol) and iodomethane (2.5 ml, 40 mmol). After stirring for 20 h at 20° C. the solid was removed by filtration and washed with THF. The combined filtrates were evaporated to dryness and triturated with dichloromethane. The solid was collected by filtration, (4.55 g, 75%). m/z (ESI+) 166 (MH⁺, 100%).

c) N-(3,5-Dibromobenzyl)-N'-(1H-imidazo[4,5-b]pyridin-2-yl)-propane-1,3-diamine Compound 1b (0.02 g) was treated with N-(3,5-dibromobenzyl)propane-1,3-diamine (0.08 g) at 125° C. under argon for 24 h. The crude product was triturated with methanol to give the title compound as a white solid (0.023 g, 50%) m/z (ESI+) 438 (MH⁺, 100%).

EXAMPLE 2

N-(4,6-Dichloro-1H-indol-2-ylmethyl)-N'-(1H-imidazo[4,5-b]pyridin-2-yl)-propane-1,3-diamine a) N-(1H-imidazo[4,5-b]pyridin-2-yl)propane-1,3-diamine
The product from 1b (4.55 g) was treated with 1,3-diaminopropane (40 ml) at reflux under argon for 50 h. The solvent was removed by evaporation under reduced pressure and the residue triturated with diethyl ether to give a brown solid. This was purified by chromatography on silica gel eluting with 5–25% (9:1 methanol/0.880 aq. ammonia) in dichloromethane to give the required product, (2.6 g, 50%)

b) N-(4,6-Dichloro-1H-indol-2-ylmethyl)-N'-(1H-imidazo[4,5-b]pyridin-2-yl)-propane-1,3-diamine Compound 2a and 4,6-dichloroindole-2-carbaldehyde were allowed to react using the general method for reductive amination on a 0.18 mmol scale to yield the title compound, as a yellow foam (0.017 g, 24%). $\delta_H$ (CD$_3$OD) 7.95 (1H, dd, J=5.2, 1.5 Hz), 7.45 (1H, dd, J=7.7, 1.5 Hz), 7.25 (1H, bs), 7.0 (1H, bs), 6.95(1H, dd, J=7.7, 5.3 Hz), 6.45 (1H, bs), 3.9 (2H, s), 3.5 (2H, t, J=6.7 Hz), 2.75 (2H, t, J=6.9 Hz), 1.9 (2H, m); m/z (ES+) 389 (26%, MH⁺), 192 (100%).

EXAMPLE 3

N-(6,8-Dibromo-1,2,3,4,-tetrahydroquinolin-4-yl)-N'-(1H-imidazo[4,5-b]pyridin-2-yl)-propane-1,3-diamine dihydrochloride To N-(1H-imidazo[4,5-b]pyridin-2-yl)propane-1,3-diamine (0.055 g, 0.29 mmol) and 6,8-dibromo-2,3,4,5- tetrahydroquinolin-4-one (0.088 g, 0.29 mmol) in methanol (2 ml) and acetic acid (0.06 g) was added sodium cyanoborohydride (0.019 g, 0.3 mmol). The reaction was then refluxed for 20 h. The reaction mixture was applied to a 2 g SCX cartridge which was flushed with MeOH (15 ml). The cartridge was then eluted with 15 ml 0.2 M $NH_3$ in MeOH, and this eluate evaporated to dryness. Further purification on silica gel eluting with 0–10% (9:1 methanol/0.880 aq. ammonia) in dichloromethane gave the title compound, which was converted to its dihydrochloride by dissolution in 1.0 M HCl in methanol (0.4 ml) and the solution evaporated to dryness to give a white solid (0.060 g, 37%); $\delta_H$ ($CD_3OD$) 8.0 (1H, dd, J=6.3, 1.2 Hz), 7.9 (1H, dd, J=6.5, 1.2 Hz), 7.55 (1H, d, J=2.2 Hz), 7.4 (1H, d, J=2.2 Hz), 7.25 (1H, dd, J=6.5, 6.3 Hz), 4.5 (1H, bs), 3.7 (2H, t, J=6.6 Hz), 3.65–3.1 (4H, m), 2.4 (1H, m), 2.2–1.95 (3H, m); m/z (ES+) 479 (6%, $MH^+$), 192 (100%).

EXAMPLE 4

N-(4,5-Dibromothien-2-ylmethyl)-N'-(1H-imidazo [4,5-b]pyridin-2-yl)-propane-1,3-diamine Using the general method for reductive amination on a 0.2 mmol scale 4,5-dibromothiophene-2-carbaldehyde was reacted with compound 2a to give the title compound as the free base, 0.037 g, 40%. m/z (ES+) 444/446/448 (28/53/30%, $MH^+$), 192 (100%).

EXAMPLE 5

N-(3,5-Dibromobenzyl)-N'-(1H-imidazo[4,5-c] pyridin-2-yl)-propane-1,3-diamine a) 1,3-Dihydroimidazo[4,5-c]pyridine-2-thione To 3,4-diaminopyridine (4.66 g, 42.75 mmol) in pyridine (40 ml) was added carbon disulfide (4 ml, 60 mmol). The mixture was heated to 60° C. for 24 h then concentrated to low volume by evaporation under reduced pressure and the residue triturated with dry tetrahydrofuran. The off white solid was collected by filtration and dried to give a first crop of 3.87 g. A second crop (0.48 g) was obtained from the filtrate (total 4.35 g, 67%). m/z (ESI+) 152 ($MH^+$, 100%).
b) 2-Methanesulfanyl-1H-imidazo[4,5-c]pyridine To compound 5a (0.38 g, 2.5 mmol) in dry DMF (10 ml) under argon was added triethylamine (0.38 ml) and iodomethane (0.163 ml). After stirring at 20° C. for 1 h the solution was concentrated by evaporation under reduced pressure and the residue triturated with diethyl ether. Purification on silica gel eluting with 0–12% (9:1 methanol/0.880 aq. ammonia) in dichloromethane gave the title compound as a white solid, 0.16 g, 39%. m/z (ESI+) 166 ($MH^+$, 100%).
c) N-(3,5-dibromobenzyl)-N'-(1H-imidazo[4,5-c]pyridin-2-yl)-propane-1,3-diamine Compound 5b (0.035 g, 0.21 mmol) was treated with N-(3,5-dibromobenzyl)propane-1, 3-diamine (0.14 g) at 140° C. under argon for 24 h. The crude product was purified by chromatography on silica gel eluting with 0–12% (9:1 methanol/0.880 aq. ammonia) in dichloromethane to give the title compound (0.055 g, 60%). m/z (ESI+) 438 ($MH^+$, 100%).

EXAMPLE 6

N-(4,6-Dichloro-1H-indol-2-ylmethyl)-N'-(1H-imidazo[4,5-b]pyrazin-2-yl)-propane-1,3-diamine dihydrochloride a) 2-Methanesulfanyl-1H-imidazo[4,5-b]pyrazine. To a solution of 1,3-dihydroimidazo[4,5-b]pyrazine-2-thione (*Aust. J. Chem.* 1982, 35, 2299–2306, 0.86 g) in aqueous NaOH (2 M, 6 ml) was added methyl iodide (0.35 ml). The resulting brown solution was stirred for 20 minutes under argon at ambient temperature. The reaction mixture was then diluted further with aqueous NaOH (2 M, 5 ml) and extracted with a small amount of $CHCl_3$. The aqueous layer was evaporated, dissolved in the minimum volume of aqueous NaOH (2 M), and acidified to pH 6.5 with HCl (conc.). The solution was then saturated with NaCl and left to crystallise for 18 h. The crystals thus obtained were collected by filtration and dried under vacuum to yield the title compound as brown crystals (0.50 g); $\delta_H$ [$(CD_3)_2SO$] 2.75 (s, 3H, $SCH_3$), 8.18 (br, s, 1H, Ar—H), 8.30 (br, s, 1H, Ar—H), 13.54 (br, s, 1H, NH); m/z (ESI+) 167 ($MH^+$, 100%).
b) N-(1H-Imidazo[4,5-b]pyrazin-2-yl)-propane-1,3-diamine. 2-Methanesulfanyl-1H-imidazo[4,5-b]pyrazine (0.49 g) and 1,3-diaminopropane (2.5 ml) were heated under reflux for 18 h to give a green solution which on cooling yielded a brown oil. The excess diaminopropane was evaporated and the residue applied to a column of silica gel eluting with 10%–15%–20% ($MeOH:NH_3$ 10:1) in $CH_2Cl_2$ to yield the title compound (0.23 g) as a white solid; $\delta_H$ ($CD_3OD$/DCl) 2.16 (m, 2H, $CH_2CH_2CH_2$), 3.12 (m, 2H, $NH_2CH_2$), 3.69 (m, 2H, $ArNHCH_2$), 8.11 (s, 2H, ArH); m/z (ESI+) 193 ($MH^+$, 100%).
c) N-(4,6-Dichloro-1H-indol-2-ylmethyl)-N'-(1H-imidazo [4,5-b]pyrazin-2-yl)-propane-1,3-diamine dihydrochloride. N-(1H-Imidazo[4,5-b]pyrazin-2-yl)-propane-1,3-diamine and 4,6-dichloro-1H-indole-2-carbaldehyde were allowed to react using the general method for reductive amination on a 0.2 mmol scale followed by hydrochloride salt formation to yield the title compound (0.017 g) as a white solid; $\delta_H$ ($CD_3OD$/DCl) 2.21 (m, 2H, $CH_2CH_2CH_2$), 3.27 (m, 2H, $ArCH_2NHCH_2$), 3.69 (m, 2H, $ArNHCH_2$), 4.48 (s, 2H, $ArCH_2$), 6.80 (m, 1H, ArH), 7.05 (m, 1H, ArH), 7.41 (m, 1H, ArH), 8.10 (s, 2H, ArH); m/z (ESI+) 390 ($MH^+$, 15%), 176 (100%).

EXAMPLE 7

N-(4,6-Dichloro-1H-indol-2-ylmethyl)-N'-(9H-purin-8-yl)-propane-1,3-diamine dihydrochloride a) 7,9-Dihydropurine-8-thione. 4,5-Diaminopyrimidine (2.0 g) was dissolved in pyridine (150 ml) containing NaOH (1.1 g) and to this solution was added carbon disulphide (2.2 ml). The reaction mixture was heated to 50° C. for 18 h. Volatiles were evaporated, the residue dissolved in $H_2O$ and acidified with HCl (conc.). The acidic mixture was warmed on a water bath and NaOH (conc.) added until precipitation was observed. This precipitate was removed by filtration. On standing at room temperature yellow crystals formed in the aqueous mother liquor which were filtered off and dried under vacuum to give the title compound (1.20 g); $\delta_H$ [$(CD_3)_2SO$] 8.45 (s, 1H, ArH), 8.69 (s, 1H, ArH), 13.02 (br, s, 1H, NH), 13.54 (br, s, 1H, NH).
b) 8-Methanesulfanyl-9H-purine: To a solution of 7,9-dihydropurine-8-thione (1.2 g) in aqueous NaOH (2 M, 8 ml) was added iodomethane (0.5 ml). The resulting brown solution was stirred for 90 minutes under argon at ambient temperature. The reaction mixture was then diluted further with aqueous NaOH (2 M, 5 ml) and extracted with $CHCl_3$ (10 ml). The aqueous layer was separated and acidified to pH 6.0 with HCl (conc.). The white precipitate thus obtained was collected by filtration and dried under vacuum to yield the title compound as a white solid (0.65 g); $\delta_H$ [$(CD_3)_2SO$] 2.74 (s, 3H, $SCH_3$), 8.75 (br, s, 1H, Ar—H), 8.85 (br, s, 1H, Ar—H), 13.48 (br, s, 1H, NH); m/z (ESI+) 167 ($MH^+$, 100%).
c) N-(9H-purin-8-yl)-propane-1,3-diamine: 8-Methanesulfanyl-9H-purine (0.65 g) and 1,3- diaminopropane (3.5 ml) were heated together under reflux for 6 h. The excess diaminopropane was then evaporated and the residue repeatedly chromatographed on silica gel eluting with (MeOH:NH$_3$ 10:1) in CH$_2$Cl$_2$ to yield the title compound (0.24 g) as a white solid; $\delta_H$ (CD$_3$OD) 1.79 (m, 2H, CH$_2$CH$_2$CH$_2$), 2.78 (m, 2H, NH$_2$CH$_2$), 3.43 (m, 2H, ArNHCH$_2$), 8.11 (s, 1H, ArH), 8.29 (s, 1H, ArH); m/z (ESI+) 193 (MH$^+$, 100%).

d) N-(4,6-Dichloro-1H-indol-2-ylmethyl)-N'-(9H-purin-8-yl)-propane-1,3-diamine dihydrochloride: N$^1$-(9H-purin-8-yl)-propane-1,3-diamine and 4,6-dichloro-1H-indole-2-carbaldehyde were allowed to react using the general method for reductive amination on a 0.2 mmol scale followed by hydrochloride salt formation to yield the title compound (0.014 g) as a white solid; $\delta_H$ (CD$_3$OD) of corresponding free base 1.81 (m, 2H, CH$_2$CH$_2$CH$_2$), 2.71 (m, 2H, ArCH$_2$NHCH$_2$), 3.44 (m, 2H, ArNHCH$_2$), 3.89 (s, 2H, ArCH$_2$), 6.38 (m, 1H, ArH), 6.91 (m, 1H, ArH), 7.18 (m, 1H, ArH), 8.12 (m, 1H, ArH), 8.42 (m, 1H, ArH); m/z (ESI+) 390 (MH$^+$, 15%), 176 (100%).

EXAMPLE 8

N-(4,5-Dibromothien-2-ylmethyl)-N'-(9H-purin-8-yl)-propane-1,3-diamine dihydrochloride N-(9H-purin-8-yl)-propane-1,3-diamine and 4,5-dibromothiophene-2-carbaldehyde were allowed to react using the general method for reductive amination on a 0.2 mmol scale followed by hydrochloride salt formation to yield the title compound (0.014 g) as a white solid; $\delta_H$ (CD$_3$OD) 2.19 (m, 2H, CH$_2$CH$_2$CH$_2$), 3.23 (m, 2H, ArCH$_2$NHCH$_2$), 3.72 (m, 2H, ArNHCH$_2$), 4.45 (s, 2H, ArCH$_2$) 7.35 (br, s, 1H, ArH), 8.56 (m, 1H, ArH), 8.95 (m, 1H, ArH); m/z (ESI+) 445 (MH$^+$, 100%).

EXAMPLE 9

N-(3-Bromo-5-methoxy-1H-indol-7-ylmethyl)-N'-(1H-imidazo[4,5-b]pyridin-2-yl)-propane-1,3-diamine a) 5-Methoxyindoline-7-carbaldehyde. 1-(tert-Butoxycarbonyl)-5-methoxyindoline (*Heterocycles*, 1992, 34, 1031; 1.75 g 7.0 mmol) was dissolved in dry THF, treated with TMEDA (1.4 ml) and cooled to −78° C. under an argon atmosphere. A solution of s-butyl lithium (1.3 M in cyclohexane, 5.18 ml) was added dropwise. After stirring at −78° C. for 1 h, the solution was treated with dry DMF (1.08 ml, 14 mmol) and stirred for a further 0.5 h. The cooling bath was then removed and the solution allowed to reach room temperature over 1 h. The reaction mixture was quenched with 10% aqueous NH$_4$Cl and the product extracted into ethyl acetate. The extracts were combined, washed with water and brine, dried (MgSO$_4$) and evaporated. The residue was chromatographed on Kieselgel 60 eluting with 0–20% ethyl acetate in hexane. Product-containing fractions were combined and evaporated to afford the title compound (510 mg); contaminated with 35% (by weight) of the corresponding N-Boc analogue; $\delta_H$ (CDCl$_3$, inter alia) 3.03 (2H, t, J=8.0 Hz, CH$_2$), 3.76 (2H, t, J=8.1 Hz, CH$_2$NH), 3.77 (3H, s, OMe), 6.42 (1H, br.s, NH), 6.73 (1H, d, J=0.8 Hz Ar—H), 6.90–6.92 (1H, m, Ar—H), 9.79 (1H, s, CHO).

b) 5-Methoxyindole-7-carbaldehyde. The product from 9a (80 mg; containing 0.3 mmol 5-methoxyindoline-7-carbaldehyde) was dissolved in dichloromethane (10 ml) and treated with MnO$_2$ (344 mg, 4.0 mmol). The reaction mixture was stirred at room temperature for 16 h, filtered through Celite and the solvent removed in vacuo. The residue was chromatographed on Kieselgel 60 eluting with 0–20% ethyl acetate in hexane to afford the title compound as a pale yellow solid (23 mg, 44%), $\delta_H$ (CDCl$_3$) 3.91(3H, s, OMe), 6.56 (1H, dd, J=2.2, 3.2 Hz, 3-H), 7.28 (1H, d, J=2.3 Hz, Ar—H), 7.33(1H, t, J=2.6 Hz, 2-H), 7.46(1H, m, Ar—H), 9.93(1H, br.s., NH), 10.07 (1H, s, CHO).

c) 3-Bromo-5-methoxyindole-7-carbaldehyde. The product from 9b (40 mg, 0.22 mmol) was dissolved in dichloromethane (5 ml), treated with N-bromosuccinimide (40 mg), and the mixture stirred at room temperature for 16 h. The solution was then diluted with dichloromethane, washed with water and brine, dried (MgSO$_4$) and evaporated. The residue was chromatographed on Kieselgel 60 eluting with 0–50% ethyl acetate in hexane. Product-containing fractions were combined and evaporated to afford the title compound as a pale pink solid (53 mg, 95%); $\delta_H$ (CDCl$_3$) 3.94 (3H, s, OMe), 7.34 (3H, s, 2-H, 4-H, 6-H), 9.93(1H, br.s. NH), 10.06 (1H, s, CHO).

d) N-(3-Bromo-5-methoxy-1H-indol-7-ylmethyl)-N'-(1H-imidazo[4,5-b]pyridin-2-yl)-propane-1,3-diamine. The product from 9c was coupled compound 2a on a 2 mmol scale using the general method for reductive amination to give the title compound as a white solid (11 mg, 13%); $\delta_H$ (CD$_3$OD) 1.89 (2H, t, J=6.8 Hz, CH$_2$), 2.75 (2H, t, J=6.8 Hz, CH$_2$), 3.47 (2H, t, J=6.6 Hz, CH$_2$), 3.82 (3H, s, OMe), 4.01 (2H, s, ArCH$_2$), 6.84 (2H, s, 2× indole-H), 6.93–6.97 (1H, m, pyr-H), 7.21 (1H, s, indole-H), 7.41 (1H, d, J=7.7 Hz, pyr-H), 7.93 (1H, d, J=5.0 Hz, pyr-H); m/z (CI$^+$) 429 (MH$^+$, 100%).

EXAMPLE 10

N-(6-Ethyl-8-iodo-1,2,3,4-tetrahydroquinolin-4-yl)-N'-(1H-imidazo[4,5-b]pyridin-2-yl)-propane-1,3-diamine dihydrochloride (a) 3-(4-Ethylphenylamino)propionic acid. To a solution of 4-ethylaniline (10 mmol) in acetonitrile (15 mL) at reflux was added 2-oxetanone (10 mmol) over a 20 minute period. After 3 h the mixture was cooled and the acetonitrile was evaporated. The residue was recrystallised from toluene to yield the title compound as a white solid; MS (ES$^-$) 385 (100%)[2M−H]$^-$, 192(76%)[M−H]$^-$.

(b) 6-Ethyl-2,3-dihydro-1H-quinolin-4-one. To phosphorus pentoxide (15 g) was added 85% orthophosphoric acid (6 mL) and the resultant mixture heated at 100° C. for 0.5 h. 3-(4-Ethylphenylamino)propionic acid (1.8 mmol) was then added. After 2 h the mixture was quenched with ice and stirred vigorously for 0.5 h. The mixture was treated with aqueous ammonia solution (pH 9.0), extracted with the ethyl acetate, dried and evaporated to give the title compound; $\delta_H$ (CDCl$_3$) 77.68(1H, d), 7.16(1H, d×d), 6.61(1H, d), 4.28(1H, br. s), 3.55(2H, t), 2.68(2H, t) 2.55(2H, q) 1.19(3H, t); MS (ES$^-$) 174(30%)[M–H]$^-$.

(c) N-(6-Ethyl-8-iodo-1,2,3,4-tetrahydroquinolin-4-yl)-N'-(1H-imidazo[4,5-b]pyridin-2-yl)-propane-1,3-diamine dihydrochloride. 6-Ethyl-8-iodo-1,2,3,4-tetrahydroquinol-4-one (140 mg, 0.47 mmol) and N-(1H-imidazo[4,5-b]pyridin-2-yl)-propane-1,3-diamine (90 mg, 0.47 mmol) were allowed to react in an identical way to Example 3 and after purification and conversion to the dihydrochloride the title compound was obtained as a white solid; $\delta_H$ (CD$_3$OD) 1.18 (3H, t), 2.07–2.16 (2H, m), 2.35–2.47 (3H, m), 3.21–3.43 (4H, m), 3.66 (2H, t), 4.42 (1H, br. s), 7.08 (1H, d), 7.26 (1H, d), 7.54 (1H, d), 7.88 (1H, dd), 7.98 (1H, dd); m/z (CI$^+$) 477 (MH$^+$, 18%).

EXAMPLE 11

N-(6,8-Dibromo-1,2,3,4-tetrahydroquinolin-4-yl)-N'-(1H-imidazo[4,5-b]pyridin-2-yl)-propane-1,3-diamine dihydrochloride—Enantiomer B (a) 6,8-Dibromo-1,2,3,4-tetrahydro-1H-quinolin-4-one O-methyloxime. A mixture of 6,8-dibromo-1,2,3,4- tetrahydroquinolin-4-one (2 mmol) in ethanol (5 mL) was added to solution of O-methylhydroxylamine hydrochloride (2.2 mmol) and sodium acetate (2.2 mmol) in water (10 mL). The resultant mixture was heated at reflux for 18 h, cooled, the solvent evaporated, and the residue partitioned between ethyl acetate and water. The organic layer was separated, dried, and evaporated to yield the title compound as pale yellow solid. m/z (ES$^+$) 374 (100%) [M+CH$_3$CN]H$^+$, 333 (80%) MH$^+$.

(b) 4-Amino-6,8-dibromo-1,2,3,4-tetrahydroquinoline. To a solution of compound 11a (1.7 mmol) in THF (20 mL) at 5° C. under an atmosphere of argon was added portionwise, with rapid stirring, zirconium tetrachloride (2.6 mmol). After 5 minutes a 2M solution of lithium borohydride (2.6 mL) in THF was added dropwise and the resultant solution was stirred at room temperature for 48 h. The mixture was treated dropwise with methanol (10 mL) and the solvent evaporated. The residue was partitioned between 2M hydrochloric acid and diethyl ether. The aqueous layer was separated, made basic by the addition of conc. ammonium hydroxide and extracted with dichloromethane. The resultant organic layer was dried and evaporated to yield the title compound as white solid. m/z (ES$^+$) 305 (2%) MH$^+$, 288 (100%) [M−NH$_3$]H$^+$.

(c) (2S)-N-(6,8-Dibromo-1,2,3,4-tetrahydroquinolin-4-yl)-2-methoxy-2-phenylacetamide—Diastereoisomer B. To a solution of compound 11b (0.6 mmol), (S)-α-ethoxyphenylacetic acid (0.7 mmol), DEC (0.7 mmol), and HOAt (0.7 mmol) in dry DMF was added N-methylmorpholine (0.7 mmol). After 16 h the solvent was evaporated and the residue partitioned between 10% citric acid solution and ethyl acetate. The organic layer was separated, washed with sodium bicarbonate solution, dried and evaporated to yield a mixture of diastereoisomeric amides as a pale yellow solid. Chromatography over silica gel eluting with petroleum ether containing ethyl acetate (30%) and collecting the slower running diastereoisomer, gave the title compound as an oil which crystallised on standing to form a white solid. δ$_H$ (CDCl$_3$) 2.01–2.10 (2H, m), 3.34 (3H, s), 3.43–3.50 (2H, m), 4.59 (1H, s), 4.66 (1H, s), 5.08–5.13 (1H, m), 6.91 (1H, d), 7.00 (1H, d), 7.26–7.43 (6H, m); m/z (ES$^+$) 453 (100%) MH$^+$.

(d) 4-Amino-6,8-dibromo-1,2,3,4-tetrahydroquinoline—Enantiomer B. Compound 11c (0.3 mmol) was dissolved in dioxane (3 mL) and 8M hydrochloric acid. After heating under reflux for 5 h the mixture was cooled and the solvent evaporated. The residue was partitioned between water/ethyl acetate and the aqueous layer separated, made basic by the addition of conc. ammonium hydroxide and extracted with dichloromethane. Drying and evaporation gave the title compound as an oil m/z. (ES$^+$) 305 (2%) MH$^+$, 288 (100%) [M−NH$_3$]H$^+$.

(e) N-(1H-imidazo[4,5-b]pyridin-2-yl)-(3,3-diethoxyprop-1-yl)amine—A mixture of 3-amino-1,1-diethoxypropane (18 mmol) and compound 1b (3.3 mmol) was heated at 130° C. under argon. After 15 h the mixture was cooled and triturated with cold diethyl ether the resultant solid was filtered off and dried to yield the title compound as a cream solid. m/z (CI$^+$) 529 (5%) [2M]H$^+$, 265 (100%) MH$^+$ (f) 3-(1H-Imidazo[4,5-b]pyridin-2-ylamino) propionaldehyde hydrochloride—Compound 11e (2 mmol) was dissolved in 1M hydrochloric acid, warmed at 100° C. for 15 minutes, cooled, and the solvent evaporated to yield the title compound as a white solid.

(g) N-(6,8-Dibromo-1,2,3,4-tetrahydroquinolin-4-yl)-N'-(1H-imidazo[4,5-b]pyridin-2-yl)-propane-1,3-diamine dihydrochloride—Enantiomer B. A mixture of compound 11f (0.13 mmol), compound 11d (0.13 mmol) and sodium acetate (0.13 mmol) was dissolved in 1% acetic acid in methanol (3 mL) for 2 h at room temperature. Sodium cyanborohydride (0.13 mmol) was added and after 20 h the solvent was evaporated and the mixture chromatographed over silica gel eluting with dichloromethane containing 8% of 1:9 ammonium hydroxide/methanol mixture. The resultant free base was converted to the title compound as a white solid; δ$_H$ (CD$_3$OD) 8.0 (1H, dd, J=6.3, 1.2 Hz), 7.9 (1H, dd, J=6.5, 1.2 Hz), 7.55 (1H, d, J=2.2 Hz), 7.4 (1H, d, J=2.2 Hz), 7.25 (1H, dd, J=6.5, 6.3 Hz), 4.5 (1H, bs), 3.7 (2H, t, J=6.6 Hz), 3.65–3.1 (4H, m), 2.4 (1H, m), 2.2–1.95 (3H, m), m/z (ES$^+$) 479 (6%, MH$^+$), ee=99% (capillary zone electrophoresis). Enantiomer B is the slower running enantiomer (by CZE on fused silica 50 cm×50 micron id, voltage 20 KV, buffer 100 nM sodium phosphate containing 40 nM cyclodextrin)

(h) N-(6,8-Dibromo-1,2,3,4-tetrahydroquinolin-4-yl)-N'-(1H-imidazo[4,5-b]pyridin-2-yl)-propane-1,3-diamine dihydrochloride—Enantiomer A. Diastereomer A of (2S)—N-(6,8-Dibromo-1,2,3,4-tetrahydroquinolin-4-yl)-2-methoxy-2-phenylacetamide was recovered via chromatography in step (c) and used to prepare Enantiomer A by a procedure analogous to steps (d)–(g).

(i) Assignment of absolute configuration of isomers of step (c). Colourless needle, 0.38×0.05×0.04 mm, orthorhombic, space group P2$_1$2$_1$2$_1$ (#19), T=150 K, α=4.8880(4) Å, b=13.7295(12) Å, c=26.441(2) Å, V=1774.4(3) Å$^3$, Z=4, D$_{calc}$=1.700 Mgm$^{-3}$, F(000)=904, μ(Cu K$_\alpha$, λ=1.54178Å)= 5.902 mm$^{-1}$, Bruker SMART 6000 diffractometer, 11989 reflections collected (6.68°≦2θ≦145.52°), 3430 unique reflections (R$_{int}$=0.0530), Gaussian absorption correction (transmission=0.37514–0.80284), full-matrix least-squares refinement (on F$^2$) of 226 variables, R1=0.0316 (wR2= 0.0789) for 3284 observed data with I≧2σ(I), R1=0.0327 (wR2=0.0805) for all data, S=1.037, w=1/[σ$^2$(F$_o^2$)+(0.0604 P)$^2$] where P=[Max(F$_o^2$,0)+2F$_c^2$]/3, residual electron density between −0.471 eÅ$^{-3}$ and 0.942 eÅ$^{-3}$, absolute structure parameter=−0.046(19).

(j). Determination of enantiomeric excess (ee) of the final products. The enantiomeric excess (ee) of the final products was determined by chiral capillary zone electrophoresis (cze) to be 98.4% for the (R)-isomer and 99.0% for the (S)-isomer. (Fused silica 50 cm×50 micron id, 20 kV, 100 mM sodium phosphate buffer pH 2.5 containing 40 mM α-cyclodextrin).

EXAMPLE 12

N-(3-Chloro-5-methoxy-1H-indol-7-ylmethyl)-N'-(1H-imidazo[4,5-b]pyridin-2-yl)-propane-1,3-diamine a) 3-Chloro-5-methoxy-1H-indol-7-carbaldehyde. 5-Methoxyindole-7-carbaldehyde 9b (40 mg, 0.22 mmol) was dissolved in dichloromethane (5 ml), treated with N-chlorosuccinimide (40 mg), and the mixture stirred at room temperature for 16 h. The solution was then diluted with dichloromethane, washed with water and brine, dried (MgSO$_4$) and evaporated to a pale brown solid.

b) N-(3-Chloro-5-methoxy-1H-indol-7-ylmethyl)-N'-(1H-imidazo[4,5-b]pyridin-2-yl)-propane-1,3-diamine. The product 12a was coupled to compound 2a on a 0.2 mmol scale using the general method for reductive amination to give the title compound as a white solid (7 mg, 9%); m/z (CI$^+$) 386 (MH$^+$, 70%).

EXAMPLE 13

N-(4,5-Dibromo-3-methylthiophen-2-ylmethyl)-N'-(1H-imidazo[4,5-c]pyridin-2-yl)propane-1,3-diamine a) N-(1H-imidazo[4,5-c]pyridin-2-yl)propane-1,3-diamine. A mixture of compound 5b (1.97 g, 10 mmol) and 1,3- diaminopropane was heated at 125° C. for 24 h. The resultant mixture was cooled and the excess reagent evaporated. The residue was chromatographed over silica gel eluting with dichloromethane/methanol/ammonium hydroxide (85:13.5:1.5) to yield the title compound. $\delta_H$ (CD$_3$OD) 8.31 (1H, s); 8.04 (1H, d); 7.25 (1H, d); 3.48 (2H, t); 2.99 (2H, t); 1.97 (2H, m).

N-(4,5-Dibromo-3-methylthiophen-2-ylmethyl)-N'-(1H-imidazo[4,5-c]pyridin-2-yl)propane-1,3-diamine. Using the general method for reductive amination a mixture of N-(3H-imidazo[4,5-c]pyridin-2-yl)propane-1,3-diamine (0.037 g, 0.19 mmol) and 4,5-dibromo-3-methylthiophene-2-carbaldehyde (0.054 g, 0.19 mmol) gave the title compound as a white solid (0.034 g, 49%). m/z (ES+) 459 (100% M$^+$).

EXAMPLE 14

N-(4,5-Dibromo-3-methylthiophen-2-ylmethyl)-N'-(5H-imidazo[4,5-c]pyridazin-6-yl)propane-1,3-diamine dihydrochloride a) [3-(5H-Imidazo[4,5-c]pyridazin-6-ylamino)propyl]carbamic acid t-butyl ester. To a solution of 1,1'-thiocarbonyldiimidazole (1.34 g, 7.5 mmol) in tetrahydrofuran (10 mL) at 0° C. under an atmosphere of argon was added dropwise, over a 15 minute period, a solution of (3-aminopropyl)carbamic acid t-butyl ester (0.87 g, 5 mmol) in tetrahydrofuran (10 mL). After stiring at RT for 3 h the mixture was evaporated and dissolved in dry dimethylformamide (10 mL) and treated with 3,4-diaminopyridazine. The resultant mixture was heated under argon at 100° C. After 48 h the mixture was cooled and the DMF evaporated. Chromatography of the crude product over silica gel eluting with dichloromethane containing increasing concentrations of 10% ammonium hydroxide/methanol (0–12%) gave the title compound as a cream coloured solid. m/z (ES+) 293 (51%, MH$^+$).

b) N-(5H-Imidazo[4,5-c]pyridazin-6-yl)propane-1,3-diamine trifluoroacetate salt. [3-(5H-Imidazo[4,5-c]pyridazin-6-ylamino)propyl]carbamic acid t-butyl ester (0.27 g, 0.92 mmol) was treated with trifluoroacetic acid (2 mL) at RT. After 2 h the mixture was evaporated, dissolved in dichloromethane, re-evaporated and dried under vacuum to yield pale yellow foam.

c) N-(4,5-Dibromo-3-methylthiophen-2-ylmethyl)-N'-(5H-imidazo[4,5-c]pyridazin-6-yl)propane-1,3-diamine dihydrochloride. Using the general method for reductive amination 4,5-dibromo-3-methylthiophene-2-carbaldehyde (0.077 g, 0.27 mmol) was reacted with N$^1$-(5H-imidazo[4,5-c]pyridazin-6-yl)propane-1,3-diamine trifluoroacetate salt (0.082 g, 0.27 mmol) to give the title compound, after conversion to the dihydrochloride with 1M methanolic hydrogen chloride. 0.027 g. m/z (AP$^+$) 459/461/463 (50/100/50%, MH$^+$).

EXAMPLE 15

N-(4,5-Dibromo-3-methylthiophen-2-ylmethyl)-N'-(1H-imidazo[4,5-b]pyridin-2-yl)propane-1,3-diamine The 4,5-dibromo-3-methylthiophene-2-carbaldehyde was coupled to compound 2a on a 0.2 mmol scale using the general method for reductive amination to give the title compound as a white solid (0.034 g, 49%). m/z (ES+) 459 (100% M$^+$).

EXAMPLE 16

N-(4-Bromo-3-methyl-5-vinylthiophen-2-ylmethyl)-N'-(5H-imidazo[4,5-c]pyridazin-6-yl)-propane-1,3-diamine a) 4-Bromo-3-methyl-5-vinylthiophene-2-carbaldehyde. A mixture of 4,5-dibromo-3-methylthiophene-2-carbaldehyde (0.14 g, 0.5 mmol) tetrakis(triphenylphosphinyl)palladium (0.062 g, 0.05 mmol) and tri-n-butylvinylstannane (0. 19 g, 0.6 mmol) in toluene was heated at 100° C. After 4 h the mixture was allowed to cool and the solvent evaporated. The crude product was chromatographed over silica gel eluting with hexane/dichloromethane (95:5) to yield the title compound. m/z (CI$^+$) 231/233 (MH$^+$, 100:100%).

b) N-(4-Bromo-3-methyl-5-vinylthiophen-2-ylmethyl)-N'-(5H-imidazo[4,5-c]pyridazin-6-yl)-propane-1,3-diamine. Using the general procedure for reductive amination with compound 14b (0.030 g, 0.096 mmol) and 4-bromo-3-methyl-5-vinylthiophene-2-carbaldehyde (0.022 g, 0.096 mmol) gave the title compound as a white solid (0.010 g, 26%). m/z (ES$^+$) 407 (100% M$^+$).

EXAMPLE 17

N-(4-Bromo-3-methyl-5-vinylthiophen-2-ylmethyl)-N'(1H-imidazo[4,5-b]pyridin-2-yl)-propane-1,3-diamine The 4-bromo-3-methyl-5-vinylthiophene-2, 16a, was coupled with compound 2a on a 0.2 mmol scale using the general method for reductive amination to give the title compound as a white solid (0.010 g, 26%). m/z (ES$^+$) 406 (100% M$^+$).

EXAMPLE 18

N-(4-Bromo-3-methyl-5-vinylthiophen-2-ylmethyl)-N'(1H-imidazo[4,5-c]pyridin-2-yl)-propane-1,3-diamine Aldehyde 16a was coupled with compound 13b on a 0.2 mmol scale using the general method for reductive amination to give the title compound as a white solid (0.010 g, 26%). m/z (ES$^+$) 406 (100% M$^+$).

EXAMPLE 19

N-(3-Bromo-2-ethoxy-5-methylsulfanybenzyl)-N'-(5H-imidazo[4,5-c]pyridazin-6-yl)propane-1,3-diamine dihydrochloride a) 3-Bromo-2-ethoxy-5-iodobenzoic acid methyl ester. A mixture of 3-bromo-2-hydroxy-5-iodobenzoic acid methyl ester (0.32 g, 0.9 mmol), potassium carbonate (0.38 g, 2.7 mmol) and iodoethane in DMF was heated at 65° C. After 48 h the mixture was cooled, evaporated to dryness and the residue partitioned between diethyl ether and water. The organic phase was separated, dried and evaporated to yield the title compound. m/z (ES$^+$) 385/387(MH$^+$, 100:100%).

b) (3-Bromo-2-ethoxy-5-iodophenyl)methanol. To a solution of 3-bromo-2-ethoxy-5-iodobenzoic acid methyl ester (0.34 g, 0.88 mmol) in dry tetrahydrofuran (5 mL) at 0° C. under argon was added a 1M THF solution of diisobutylaluminium hydride (5.3 mL). After 6 h the mixture was evaporated and partitioned between ethyl acetate and 1M hydrochloric acid. The organic layer was separated, dried and evaporated to yield the title compound. m/z (ES$^+$) 379/381(MNa$^+$, 100:100%).

c) 3-Bromo-2-ethoxy-5-iodobenzaldehyde. To a solution of (3-bromo-2-ethoxy-5-iodophenyl)methanol (0.36 g, 0.78 mmol) in dichloromethane was added maganese dioxide (0.068 g, 7.85 mmol) After stirring at RT for 3 h the mixture was filtered and the solvent evaporated. The crude product was chromatographed over silica gel eluting with hexane/dichloromethane (1:1) to yield the title compound. $\delta_H$ (CDCl$_3$) 10.26 (1H, s); 8.10 (1H, d); 8.07 (1H, d); 4.15 (2H, q); 1.49 (3H, t).

d) 2-(3-Bromo-2-ethoxy-5-iodophenyl)-1,3-dioxolane. A solution of 3-bromo-2-ethoxy-5-iodobenzaldehyde (0.58 g, 1.63 mmol), 1,2-dihydroxyethane (0.11 g, 1.8 mmol) and 4-toluenesulfonic acid monohydrate (0.01 g) in toluene (40 mL) was heated at reflux with separation of water. After 14 h the mixture was cooled and the solvent evaporated. The residue was partitioned between ethyl acetate and aqueous sodium bicarbonate solution. The organic layer was separated, dried and evaporated to yield the title compound. m/z (ES$^+$) 398/400 (M$^+$, 100:100%).

e) 2-(3-Bromo-2-ethoxy-5-methylsulfanylphenyl)-1,3-dioxolane. A mixture of 2-(3-bromo-2-ethoxy-5-iodophenyl)-1,3-dioxalane (0.43 g, 3.0 mmol), copper (I) oxide (0.095 g, 1.35 mmol) and sodium thiomethoxide (0.09 g, 0.23 mmol) was heated at 80° C. After 48 h the mixture was cooled, filtered and the solvent evaporated. The residue was partitioned between water/diethyl ether the organic layer separated, dried and evaporated to yield the title compound. m/z (CI$^+$) 319/321 (MH$^+$, 100:100%).

f) 3-Bromo-2-ethoxy-5-methysulfanylbenzaldehyde. A solution of 2-(3-bromo-2-ethoxy-5-methylsulfanylphenyl)-1,3-dioxalane (0.097 g, 0.3 mmol) and pyridinium toluene-sufonate (0.038 g, 0.15 mmol) in acetone (10 mL) containing water (1 drop) was heated at reflux. After 20 h the mixture was cooled, evapoarated and the residue partitioned between diethyl ether/aqueous sodium bicarbonate solution. The organic phase was separated, dried and evaporated to yield the title compound. $\delta_H$ (CDCl$_3$) 10.30 (1H, s); 7.67 (1H, s); 7.44 (1H, d); 4.15 (2H, q); 2.50 (3H, s); 1.48 (3H, t).

g) N-(3-Bromo-2-ethoxy-5-methylsulfanybenzyl)-N'-(5H-imidazo[4,5-c]pyridazin-6-yl)propane-1,3-diamine dihydrochloride. Using the general method for reductive amination 3-bromo-2-ethoxy-5-methysulfanylbenzaldehyde (0.05 g, 0.18 mmol) was reacted with compound 14b (0.055 g, 0.182 mmol) to give the title compound, after conversion to the dihydrochloride with 1M methanolic hydrogen chloride. 0.035 g. m/z (AP$^+$) 451/453 (100/100% MH$^+$).

EXAMPLE 20

N-(6-Chloro-8-iodochroman-4-yl)-N'-(5H-imidazo[4,5-c]pyridazin-6-yl)propane-1,3-diamine Using the method described in Example 3 6-chloro-8-iodochromanone (0.05 g, 0.27 mmol) was reacted with compound 14b (0.035 g, 0.11 mmol) to give the title compound. 0.007 g,. m/z (AP$^+$) 480/482(100/35%, MH$^+$).

EXAMPLE 21

N-(3-Chloro-5-methoxy-1H-indol-7-ylmethyl)-N'-(5H-imidazo[4,5-c]pyridazin-6-yl)propane-1,3-diamine dihydrochloride Using the general method for reductive amination, aldehyde 12a (0.018 g, 0.09 mmol) was reacted with compound 14b (0.028 g, 0.09 mmol) to give the title compound, after conversion to the dihydrochloride with 1M methanolic hydrogen chloride. 0.015 g,. m/z (AP$^+$) 386/388 (100/35%, MH$^+$).

EXAMPLE 22

N-(4,5-Dibromo-3-methylthiophen-2-ylmethyl)-N'-(1H-thieno[3,4-d]imidazol-2-yl)propane-1,3-diamine a) 3,4-Diaminothiophene. To a suspension of 2,5-dibromo-3,4-dinitrothiophene (10 g, 30.12 mmol) in conc. HCl (294 mL) was added portionwise tin (21.2 g, 178 mmol) keeping the temperature below 30° C. The mixture was stirred for 4 h at room temperature then stored in the fridge for two days. The solid was collected by filtration, washed with diethyl ether and acetone then suspended in water (60 mL) and diethylether (60 mL). The mixture was cooled in an ice-bath, then made alkaline using 4M NaOH. The aqueous phase was separated then continuously extracted with diethyl ether. The organic phases were combined then concentrated to give 2.3 g of the title compound as a beige solid; $\delta_H$ (CDCl$_3$) 6.1 (2H, s), 3.3 (4H, bs).

b) {3-[3-(4-Aminothiophen-3-yl)thioureido]propyl}carbamic acid tert-butyl ester. The product from 22a (0.421 g, 3.7 mmol) was dissolved in dichloromethane (13 mL) and treated with diisopropylethylamine (892 uL, 5.14 mmol), 4-dimethylaminopyridine (0.125 g, 1 mmol) and (3-isothiocyanato-propyl)carbamic acid tert-butyl ester (1.14 g, 5.28 mmol). The reaction mixture was stirred at room temperature for 16 h, loaded on Kieselgel 60 and chromatographed eluting with 0–2% (9:1 MeOH/20 M NH$_3$) in dichloromethane. The fractions containing the title compound were combined and concentrated, the residue was re-chromatographed on Kieselgel 60 eluting with 0–50% ethyl acetate in hexane. The fractions containing the title compound were combined and concentrated, the residue was applied to a 10 g Varian Bond Elute SCX cartridge which was flushed with methanol. The cartridge was then eluted with 0.2 M NH$_3$ in methanol, and this eluate evaporated to dryness to afford the title compound as a pale yellow oil (0.26 g, 21%), m/z (CI$^+$) 331 (MH$^+$, 10%).

c) [3-(1H-Thieno[3,4-d]imidazol-2-ylamino)propyl]carbamic acid tert-butyl ester. The product from 22b (0.180 g, 0.54 mmol) was dissolved in dimethylformamide (40 mL) and treated with triethylamine (76 uL, 0.54 mmol) and mercuric chloride (0.149 g, 0.54 mmol). The reaction mixture was stirred at room temperature for 16 h then diluted with ethyl acetate and filtered through celite. The filtrate was concentrated and the residue chromatographed on Kieselgel 60 eluting with 0–10% (9:1 MeOH/20 M NH$_3$) in CH$_2$Cl$_2$ to afford the title compound as a brown oil (0.050 g, 31%), m/z (CI$^+$) 297 (MH$^+$, 100%).

d) N-(1H-Thieno[3,4-d]imidazol-2-yl)propane-1,3-diamine bistrifluoroacetate salt. The product from 22c (0.045 g, 0.15 mmol) was dissolved in trifluoroacetic acid (2 mL). The reaction mixture was stirred at room temperature for 0.5 h then concentrated to afford the title compound as a brown oil (0.056 g, 88%), m/z (CI$^+$) 197 (MH$^+$, 80%), 393 (2MH$^+$, 100%).

e) N-(4,5-Dibromo-3-methylthiophen-2-ylmethyl)-N'-(1H-thieno[3,4-d]imidazol-2-yl)propane-1,3-diamine. The product from 22d was coupled to 4,5-dibromo-3-methylthiophene-2-carbaldehyde on a 0.09 mmol scale using the general method for reductive amination to give the title compound as a pink solid (0.015 g, 36%), m/z (CI$^+$) 465 (MH$^+$, 100%).

EXAMPLE 23

N-(4-Bromo-3-methyl-5-vinylthiophen-2-ylmethyl)-N'-(1H-thieno[3,4-d]imidazol-2-yl)propane-1,3-diamine The product from 22d was coupled to aldehyde 16a on a 0.09 mmol scale using the general method for reductive amination to give the title compound as a pink solid (0.015 g, 36%), m/z (CI$^+$) 411 (MH$^+$, 100%).

EXAMPLE 24

N-(3-Chloro-5-methoxy-1H-indol-7-ylmethyl)-N'-(1H-thieno[3,4-d]imidazol-2-yl)propane-1,3-diamine The product from 19d was coupled to compound 12a on a 0.13 mmol scale using the general method for reductive amination to give the title compound as a beige solid (0.038 g, 73%), m/z (CI$^+$) 390 (MH$^+$, 70%).

EXAMPLE 25

N-(4-Bromo-5-difluoromethyl-3-methylthiophen-2-ylmethyl)-N'-(1H-imidazo[4,5-b]pyridin-2-yl)propane-1,3-diamine dihydrochloride a) 2-(4,5-Dibromo-3-methylthiophen-2-yl)-1,3-dioxolane. A solution of 4,5-dibromo-3-methylthiophene-2-carbaldehyde (2.84 g, 10 mmol), 1,2-dihydroxyethane (1.36 g, 22 mmol) and resin supported 4-toluenesulfonic acid in toluene (100 mL) was heated at reflux with separation of water. After 3 h the mixture was cooled, filtered and the solvent evaporated to yield the title compound (3.28 g); m/z (AP$^+$) 329 (MH$^+$, 100%).

b) 3-Bromo-5-(1,3-dioxolan-2-yl)-4-methylthiophene-2-carbaldehyde. Compound 25a (3.28 g, 10 mmol) was dissolved in dry THF (40 mL) and cooled to −78° C. under an argon atmosphere. A solution of n-butyl lithium (2.5 M in cyclohexane, 4 mL) was added dropwise. After stirring at −78° C. for 0.3 h, the solution was treated with dry DMF (0.775 mL, 10 mmol) and stirred for a further 0.6 h. The cooling bath was then removed and the solution allowed to reach room temperature over 3 h. The reaction mixture was quenched with 2N aqueous HCl and the product extracted into dichloromethane. The extracts were combined, dried (MgSO$_4$) and evaporated to yield the title compound (2.4 g); $\delta_H$ (CDCl$_3$) 2.29 (3H, s, CH$_3$), 4.07 (4H, m, CH$_2$CH$_2$), 6.14 (1H, s, CH), 9.98 (1H, s, CHO).

c) 2-(4-Bromo-5-difluoromethyl-3-methylthiophen-2-yl)-1,3-dioxolane. A solution of compound 25b (0.277 g, 1 mmol) and deoxofluor (0.378 g, 1.7 mmol) in dichloromethane (1 ml) was heated at reflux. After 14 h the mixture was diluted with dichloromethane, washed successively with aqueous sodium bicarbonate and 1N aqueous HCl, dried (MgSO$_4$) and evaporated to yield the title compound (0.28 g); $\delta_H$ (CDCl$_3$) 2.25 (3H, s, CH$_3$), 4.06 (4H, m, CH$_2$CH$_2$), 6.12 (1H, s, CH), 6.87 (1H, t, J=54.8 Hz, CHF$_2$).

d) 4-Bromo-5-difluoromethyl-3-methylthiophene-2-carbaldehyde. A solution of compound 25c (0.598 g, 2 mmol) and resin supported 4-toluenesulfonic acid in acetone (20 mL) containing water (1 mL) was stirred at room temperature. After 14 h the mixture was filtered and the solvent evaporated to yield the title compound (0.365 g); $\delta_H$ (CDCl$_3$) 2.56 (3H, s, CH$_3$), 6.90 (1H, t, J=56 Hz, CHF$_2$), 10.07 (1H, s, CHO).

e) N-(4-Bromo-5-difluoromethyl-3-methylthiophen-2-ylmethyl)-N'-(1H-imidazo[4,5-b]pyridin-2-yl)propane-1,3-diamine dihydrochloride. Using the general method for reductive amination, compound 25d (0.074 g, 0.29 mmol) was reacted with compound 2a (0.056 g, 0.29 mmol) to give the title compound, after conversion to the dihydrochloride with 1M methanolic hydrogen chloride (0.043 g); m/z (AP$^+$) 430 (MH$^+$, 100%).

EXAMPLE 26

N-(4-Bromo-5-difluoromethyl-3-methylthiophen-2-ylmethyl)-N'-(5H-imidazo[4,5-c]pyridazin-6-yl)propane-1,3-diamine dihydrochloride Using the general method for reductive amination, compound 25d (0.074 g, 0.29 mmol) was reacted with compound 14b (0.29 mmol) to give the title compound, after conversion to the dihydrochloride with 1M methanolic hydrogen chloride (0.037 g); m/z (AP$^+$) 431 (MH$^+$, 100%).

EXAMPLE 27

N-(4-Bromo-5-difluoromethyl-3-methylthiophen-2-ylmethyl)-N'-(1H-thieno[3,4-d]imidazol-2-yl)propane-1,3-diamine dihydrochloride Using the general method for reductive amination, compound 25d (0.061 g, 0.24 mmol) was reacted with compound 19d (0.24 mmol) to give the title compound, after conversion to the dihydrochloride with 1M methanolic hydrogen chloride (0.044 g); m/z (AP$^+$) 435 (MH$^+$, 100%).

EXAMPLE 28

N-(4-Bromo-3-methyl-5-trifluoromethylthiophen-2-ylmethyl)-N'-(5H-imidazo[4,5-c]pyridazin-6-yl)propane-1,3-diamine dihydrochloride a) 4-Bromo-3-methyl-5-trifluoromethylthiophene-2-carbaldehyde. 4,5-Dibromo-3-methylthiophene-2-carbaldehyde (250 mg, 0.88 mmol) was dissolved in a mixture of DMF (10 mL) and N-methylpyrrolidine (0.5 mL) containing copper (I) iodide (200 mg, 0.96 mmol) and 2,2-difluoro-2-fluorosulfonyl acetic acid methyl ester (871 mg, 4.4 mmol). After heating at 70° C. with vigorous stirring for 7 h the mixture was cooled and allowed to cool to room temperature overnight. The DMF was evaporated and the residue was partitioned between diethyl ether (30 mL) and saturated ammonium chloride solution. The organic layer was separated, washed with brine, dried and evaporated to yield the crude product. Filtration through silica gel eluting with hexane/diethyl ether (1:1) gave the title compound as a pale yellow solid (155 mg); m/z (AP$^-$) 272 (M$^-$, 25%).

b) N-(4-Bromo-3-methyl-5-trifluoromethylthiophen-2-ylmethyl)-N'-(5H-imidazo[4,5-c]pyridazin-6-yl)propane-1,3-diamine dihydrochloride. Using the general method for reductive amination, purification and salt formation, compound 28a was reacted with compound 14b to give the title compound (23 mg); m/z (AP$^+$) 449 (MH$^+$, 100%).

EXAMPLE 29

N-(4-Bromo-3-methyl-5-trifluoromethylthiophen-2-ylmethyl)-N'-(1H-thieno[3,4-d]imidazol-2-yl)propane-1,3-diamine dihydrochloride Using the general method for reductive amination, compound 28a (0.066 g, 0.24 mmol) was reacted with compound 19d (0.24 mmol) to give the title compound, after conversion to the dihydrochloride with 1 M methanolic hydrogen chloride (0.010 g); m/z (AP$^+$) 453 (MH$^+$, 100%).

EXAMPLE 30

N-(4-Bromo-3-methyl-5-trifluoromethylthiophen-2-ylmethyl)-N'-(1H-imidazo[4,5-b]pyridin-2-yl)propane-1,3-diamine dihydrochloride Using the general method for reductive amination, compound 28a (0.066 g, 0.24 mmol) was reacted with compound 2a (0.24 mmol) to give the title compound, after conversion to the dihydrochloride with 1M methanolic hydrogen chloride (0.012 g); m/z (AP$^+$) 448 (MH$^+$, 100%).

EXAMPLE 31

N-(4-Bromo-3-methyl-5-trifluoromethylthiophen-2-ylmethyl)-N'-(1H-imidazo[4,5-c]pyridin-2-yl)propane-1,3-diamine dihydrochloride Using the general method for reductive amination, compound 28a (0.066 g, 0.24 mmol) was reacted with compound 13a (0.24 mmol) to give the title compound, after conversion to the dihydrochloride with 1M methanolic hydrogen chloride (0.010 g); m/z (AP$^+$) 448 (MH$^+$, 100%).

EXAMPLE 32

N-(4-Bromo-5-(1-fluorovinyl)-3-methylthiophen-2-ylmethyl)-N'-(1H-imidazo[4,5-b]pyridin-2-yl)propane-1,3-diamine hydrochloride a) 4-Bromo-3-methyl-5-vinyl-thiophene-2-carbaldehyde. A solution of 4,5-dibromo-3-methylthiophene-2-carbaldehyde (1.42 g, 5 mmol), tetrakis(triphenylphosphine)-palladium(0) (0.622 g, 0.5 mmol) and tributylvinyltin (1.75 mL, 6 mmol) in toluene (50 mL) was heated at 100° C. After 14 h the reaction mixture was concentrated and the residue was chromatographed on Kieselgel 60 eluting with 0–50% dichloromethane in hexane to afford the title compound (0.623 g); m/z (AP$^+$) 231 (MH$^+$, 100%).

b) 4-Bromo-5-(2-bromo-1-hydroxyethyl)-3-methylthiophene-2-carbaldehyde. A solution of compound 32a (0.42 g, 1.82 mmol) in dimethylsulfoxide (2.1 mL) was treated successively with water (0.067 mL, 3.64 mmol) and N-bromosuccinimide (0.647 g, 3.64 mmol). After 0.5 h, aqueous sodium bicarbonate was added and the product extracted with ethyl acetate. The extracts were combined, dried (MgSO$_4$) and evaporated. The residue was chromatographed on Kieselgel 60 eluting with 0–4% ethyl acetate in dichloromethane to afford the title compound (0.375 g); $\delta_H$ (CDCl$_3$) 2.54 (3H, s, CH$_3$), 2.97 (1H, d, J=3.8 Hz, OH), 3.54 (1H, dd, J=8.6, 10.6 Hz, CH$_2$Br), 3.82 (1H, dd, J=3.1, 8.6 Hz, CH$_2$Br), 5.27 (1H, m, CHOH), 10.07 (1H, s, CHO).

c) 4-Bromo-5-(1-fluorovinyl)-3-methylthiophene-2-carbaldehyde

Method A. Diphenyl(1-fluorovinyl)methylsilane. In a flame-dried 1 L 3-neck round bottom under an anhydrous atmosphere, 65 mL (309 mmol) of diphenylmethylchlorosilane was added to 4.3 g (618 mmol) of lithium wire in 650 mL of anhydrous THF. The mixture was stirred at ambient temperature for 20 hours. The mixture was then cooled to −78° C. and the atmosphere replaced with 1,1-difluoroethylene (excess) such that the temperature of the reaction mixture remained below −55° C. Difluoroethylene addition was stopped when the reaction temperature remained at or below −70° C. The reaction was stirred at <−70° C. until it turned a clear light yellow (~2 hr.) and was then allowed to warm to ambient temperature. The remaining lithium wire was removed and the mixture treated with portions of Na$_2$SO$_4$-10H$_2$O until no gas evolved upon addition. The mixture was then dried over Na$_2$SO$_4$, filtered through a silica pad and the pad rinsed with ether. The combined filtrates were dried under vacuum, the resulting residue suspended/dissolved in hexanes and filtered through another silica pad. The pad was rinsed with hexanes, the filtrates combined and the solvent removed under reduced pressure to give a light yellowish liquid with some white crystalline material present. The product was purified by vacuum distillation (113–117° C. at ~2 Torr) to give 44 g (59%) of the title compound as a clear colorless liquid. $\delta_H$ (CDCl$_3$): 0.72 (3H, s, CH$_3$), 4.85 (1H, dd, J=2.6, 61.2 Hz, CH$_2$), 5.48 (1H, dd, J=2.6, 33.3, CH$_2$), 7.39 (6H, m, ArH), 7.59 (4H, d, J=6.8 Hz, ArH); $\delta_F$ (CDCl$_3$): −103.16 (q, dd, J=33.3, 61.2 Hz).

b) 4-Bromo-5-(1-fluorovinyl)-3-methylthiophene-2-carbaldehyde. Under an inert atmosphere in a 25 mL round bottom flask were combined 166 mg of Diphenyl(1-fluorovinyl)methylsilane (0.685 mmol), 130 mg of 4,5-dibromo-3-methylthiophene-2-carbaldehyde (0.459 mmol), 209 mg of CsF (1.38 mmol), 88 mg of CuI (0.459 mmol), 10.5 mg Pd$_2$(dba)$_3$ (0.0115 mmol) and 14.1 mg AsPh$_3$ (0.0459 mmol). The flask containing the solids was cooled to ~0° C. with an ice bath and 2 mL of degassed, anhydrous dimethylformamide (DMF) were added. The reaction mixture was stirred at 0 to 5° C. for 2 hr and then 2 mL of water was added. The mixture was then diluted with 5 mL 1N NaOH and extracted with 25% diethyl ether/hexanes (4×20 mL). The combined extracts were washed with brine (1×5 mL), dried over Na$_2$SO$_4$, and the solvent removed under vacuum. The remaining residue was purified by flash silica gel chromatography (CH$_2$Cl$_2$/hexanes) to give a 50% yield of the title compound as a white solid. $\delta_H$(CDCl$_3$) 2.57 (3H, s, CH$_3$), 5.24 (1H, dd, J=4.0, 18.5 Hz, CH$_2$), 5.70 (1H, dd, J=4.0, 49.6 Hz, CH$_2$), 10.06 (1H, s, CHO); $\delta_H$ (CDCl$_3$): −92.20 (q, dd, J=18.4, 50.4 Hz); m/z (ESI$^+$) (MH$^+$, 249).

Method B. A solution of compound 32b (0.384 g, 1.16 mmol) in dry dichloromethane (6 mL) was cooled to −78° C. A solution of deoxofluor (0.282 g, 1.27 mmol) in dry dichloromethane (4 mL) was added. After 3 h the mixture was diluted with dichloromethane, washed with aqueous sodium bicarbonate, dried (MgSO$_4$) and evaporated. The residue was dissolved in benzene (15 mL) and treated with DBU (0.1 g, 0.66 mmol). After 2 h the reaction mixture was concentrated, the residue was diluted with dichloromethane and washed with 1M aqueous HCl. The organic phase was dried (MgSO$_4$) and concentrated to yield the title compound (0.133 g); $\delta_H$ (CDCl$_3$) 2.57 (3H, s, CH$_3$), 5.23 (1H, dd, J=4.0, 18.5 Hz, CH$_2$), 5.70 (1H, dd, J=4.0, 49.9 Hz, CH$_2$), 10.04 (1H, s, CHO).

d) N-(4-Bromo-5-(1-fluorovinyl)-3-methylthiophen-2-ylmethyl)-N'-(1H-imidazo[4,5-b]pyridin-2-yl)propane-1,3-diamine hydrochloride. Using the general method for reductive amination, compound 32c (0.075 g, 0.3 mmol) was reacted with compound 2a (0.057 g, 0.3 mmol) to give the title compound, after conversion to the hydrochloride with 1M methanolic hydrogen chloride (0.026 g); m/z (AP$^+$) 424 (MH$^+$, 100%).

EXAMPLE 33

N-(4-Bromo-5-(1-fluorovinyl)-3-methylthiophen-2-ylmethyl)-N'-(1H-imidazo[4,5-c]pyridin-2-yl)propane-1,3-diamine Using the general method for reductive amination, compound 32c (0.075 g, 0.3 mmol) was reacted with compound 13a (0.057 g, 0.3 mmol) to give the title compound (0.025 g); m/z (AP$^+$) 424 (MH$^+$, 100%).

EXAMPLE 34

N-(4-Bromo-5-(1-fluorovinyl)-3-methylthiophen-2-ylmethyl)-N'-(5H-imidazo[4,5-c]pyridazin-6-yl)propane-1,3-diamine Using the general method for reductive amination, compound 32c (0.066 g, 0.27 mmol) was reacted with compound 14b (0.27 mmol) to give the title compound (0.022 g); m/z (AP$^+$) 425 (MH$^+$, 100%).

EXAMPLE 35

N-(4-Bromo-5-(1-fluorovinyl)-3-methylthiophen-2-ylmethyl)-N'-(1H-thieno[3,4-d]imidazol-2-yl)propane-1,3-diamine Using the general method for reductive amination, compound 32c (0.059 g, 0.24 mmol) was reacted with compound 19d (0.24 mmol) to give the title compound (0.025 g); m/z (AP$^+$) 429 (MH$^+$, 100%).

EXAMPLE 36

N-(4-Bromo-3-methyl-5-ethynylthiophen-2-ylmethyl)-N'-(5H-imidazo[4,5-c]pyridazin-6-yl)propane-1,3-diamine a) 4-Bromo-5-ethynyl-3-methylthiophene-2-carbaldehyde. A mixture of trimethylsilylacetylene (3.7 mL, 26.4 mmol), 4,5-dibromo-3-methylthiophene-2-carbaldehyde (1.50 g, 52.8 mmol), copper (I) iodide (19 mg) and bis (triphenylphosphine)palladium (II) chloride (80 mg) in triethylamine (35 mL) was stirred at room temperature. After 2 h the mixture was filtered and evaporated. The crude product was chromatographed over silica gel eluting with petroleum ether 40–60 containing increasing concentrations of dichloromethane up to 50%. The resultant trimethylsilyl protected acetylene was treated with methanol containing 10% concentrated ammonium hydroxide. After stirring at 20° C. for 15 minutes the solvent was evaporated to yield the title compound as a light brown foam (0.73 g); $\delta_H$ (CDCl$_3$) 9.99 (1H, s), 3.80 (1H, s), 2.55 (3H, s).

b) N-(4-Bromo-3-methyl-5-ethynylthiophen-2-ylmethyl)-N'-(5H-imidazo[4,5-c]pyridazin-6-yl)propane-1,3-diamine. Using the general method for reductive amination and purification, compound 36a was reacted with compound 14b (0.24 mmol) to give the title compound (21 mg); m/z (AP$^+$) 405 (MH$^+$, 100%).

EXAMPLE 37

N-(4-Bromo-3-methyl-5-ethynylthiophen-2-ylmethyl)-N'-(1H-imidazo[4,5-b]pyridin-2-yl)propane-1,3-diamine Using the general method for reductive amination and purification, compound 36a was reacted with compound 2a (0.24 mmol) to give the title compound (19 mg); m/z (AP$^+$) 404 (MH$^+$, 100%).

EXAMPLE 38

N-(4-Bromo-3-methyl-5-ethynylthiophen-2-ylmethyl)-N'-(1H-imidazo[4,5-c]pyridin-2-yl)propane-1,3-diamine Using the general method for reductive amination and purification, compound 36a was reacted with compound 13a (0.24 mmol) to give the title compound (23 mg); m/z (AP$^+$) 404 (MH$^+$, 100%).

EXAMPLE 39

N-(4-Bromo-3-methyl-5-ethynylthiophen-2-ylmethyl)-N'-(1H-thieno[3,4-d]imidazol-2-yl)propane-1,3-diamine Using the general method for reductive amination and purification, compound 36a was reacted with compound 19d (0.24 mmol) to give the title compound (23 mg); m/z (AP$^+$) 409 (MH$^+$, 100%).

EXAMPLE 40

N-(4-Bromo-5-ethyl-3-(1-propynyl)thiophen-2-ylmethyl)-N'-(5H-imidazo[4,5-c]pyridazin-6-yl)propane-1,3-diamine dihydrochloride a) 3,4-Dibromo-5-ethylthiophene-2-carbaldehyde. 2,3,4-Tribromo-5-ethylthiophene (1.4 g, 4.1 mmol) was dissolved in dry THF (40 mL) and cooled to −78° C. under an argon atmosphere. A solution of n-butyl lithium (1.6 M in cyclohexane, 2.56 mL) was added dropwise. After stirring at −78° C. for 0.5 h, the solution was treated with dry DMF (0.32 mL, 4.1 mmol) and stirred for a further 0.6 h. The cooling bath was then removed and the solution allowed to reach room temperature over 3 h. The reaction mixture was quenched with 2M aqueous HCl and the product extracted into dichloromethane. The extracts were combined, dried (MgSO$_4$) and evaporated. The residue was chromatographed on Kieselgel 60 eluting with 0–50% dichloromethane in hexane to yield the title compound (0.6 g); m/z (AP$^+$) 299 (MH$^+$, 100%).

b) 4-Bromo-3-(1-propynyl)-5-ethylthiophene-2-carbaldehyde. Methyl acetylene was bubbled into a solution containing triethylamine (2 ml) and THF (2 ml). After 10 min the solution was quickly added to a 10 mL reactor vessel containing compound 40a (0.227 g, 0.8 mmol), bis (triphenylphosphine)palladium (II) chloride (5.8 mg, 0.008 mmol) and copper (I) iodide (0.15 mg, 0.0008 mmol). The reactor was sealed and the reaction mixture stirred at room temperature. After 60 h, the reaction mixture was filtered through celite and concentrated. The residue was chromatographed on Kieselgel 60 eluting with 0–50% dichloromethane in hexane to yield the title compound (0.126 g); m/z (AP$^+$) 257 (MH$^+$, 100%).

c) N-(4-Bromo-5-ethyl-3-(1-propynyl)thiophen-2-ylmethyl)-N'-(5H-imidazo[4,5-c]pyridazin-6-yl)propane-1, 3-diamine dihydrochloride. Using the general method for reductive amination, compound 40b (0.051 g, 0.2 mmol) was reacted with compound 14b (0.2 mmol) to give the title compound, after conversion to the dihydrochloride with 1M methanolic hydrogen chloride (0.024 g); m/z (AP$^+$) 433/435 (MH$^+$, 100%).

EXAMPLE 41

N-(4-Bromo-5-ethyl-3-(1-propynyl)thiophen-2-ylmethyl)-N'-(1H-imidazo[4,5-c]pyridin-2-yl)propane-1,3-diamine Using the general method for the synthesis of example 40.

EXAMPLE 42

N-(4-Bromo-5-ethyl-3-(1-propynyl)thiophen-2-ylmethyl)-N'-(1H-imidazo[4,5-b]pyridin-2-yl)propane-1,3-diamine Using the general method for the synthesis of example 40.

EXAMPLE 43

N-(4-Bromo-5-ethyl-3-(N-propynyl)thiophen-2-ylmethyl)-N'-(1H-thieno[3,4-d]imidazol-2-yl)propane-1,3-diamine Using the general method for the synthesis of example 40.

Biological Data

1. Enzyme Inhibition (*S. aureus* MRS)—aminoacylation Assay

Compounds of the present invention may be assayed for their ability to inhibit the enzyme methionyl tRNA synthetase (MRS), using recombinant *S. aureus* MRS, as follows:

| Reaction Mix (per 1 ml) | | |
|---|---|---|
| Stock | Volume ($\mu$l) | Final Concentration |
| 100 mM Tris/Cl, pH 7.9 | 600 | 30 mM |
| 250 mM KCl | | 75 mM |
| 125 mM ATP | 40 | 2.5 mM |
| 250 mM MgCl$_2$ | 80 | 10 mM |
| 50 mM DTT | 80 | 2 mM |
| 1 mM Met (H-3 hot and cold) | 40 | 10 uM |

-continued

Reaction Mix (per 1 ml)

| Stock | Volume (µl) | Final Concentration |
|---|---|---|
| Solid tRNA (Mixed E. coli MRE 600) | 4 mg/ml | 2 mg/ml |
| H₂O | 160 | |
| 10 × Inhibitor (0–10 µM) | 5 µl per well | 0–1 µM |

The reaction is started by adding 20 µl appropriately diluted pure enzyme (pre-incubated with inhibitor) to 25 µl reaction mix for 10 min at room temperature. The reaction is terminated by the addition of 150 µl 167 mM sodium citrate, pH 2.15 containing phosphodiesterase (PDE) SPA beads (0.833 mg/ml). The binding of the radiolabelled product to the bead brings the isotope into close enough proximity to allow radiation from the tritium to excite the scintillant within the bead. Any unbound radiolabel is not close enough to the scintillant to allow this energy transfer, so no signal is generated. Following termination of the reaction, plates are spun at 2500 rpm for 5 min in a Mistral 3000E plate centrifuge (or alternatively allowed to stand for 1 hour). The assay is conducted in 96-well Optiplates (Packard). Plates are counted on a TopCount. (Packard 96 well counter).

Reagents

Mixed E. coli MRE 600 tRNA and ATP were purchased from Boehringer-Mannheim, L-[methyl-³H]methionine and phosphodiesterase scintillation proximity (SPA) beads from Amersham Pharmacia Biotech and other reagents from Sigma.

Pure recombinant S. aureus MRS (EP application number 97300317.1, SmithKline Beecham) was obtained using standard purification procedures. The enzyme is diluted in Dilution Buffer which consists of 10 mM Tris/Cl, 2 mM DTT pH 7.9.

Results

Examples 1 to 7, 9, 11, 12, 15, 17, 22–30, 32, 34–37, 39–41, and 43–44 have $IC_{50}$ values against S. aureus MRS in the range <3 to 200 nM. All are highly selective with respect to the mammalian enzyme (no inhibition of rat MRS up to 1 µM).

2. Enzyme Inhibition (H. influenzae MRS)—aminoacylation Assay

Compounds of the present invention may be assayed for their ability to inhibit the enzyme methionyl tRNA synthetase (MRS), using recombinant H. influenzae MRS (R. D. Fleischmann et al., Science, 269, 496–512, 1995), as follows:

Reaction Mix (per 1 ml)

| Stock | Volume (µl) | Final Concentration |
|---|---|---|
| 100 mM Tris/Cl, pH 7.9 | 600 | 30 mM |
| 250 mM KCl | | 75 mM |
| 125 mM ATP | 40 | 2.5 mM |
| 250 mM MgCl₂ | 80 | 10 mM |
| 50 mM DTT | 80 | 2 mM |
| 1 mM Met (H-3 hot and cold) | 20 | 10 µM |
| Solid tRNA (Mixed E. coli MRE 600) | 4 mg/ml | 2 mg/ml |
| H₂O | 180 | |
| 10 × Inhibitor (0–100 µM) | 5 µl per well | 0–10 µM |

The reaction is started by adding 20 µl appropriately diluted pure enzyme (pre-incubated with inhibitor) to 25 µl reaction mix for 10 min at room temperature. The reaction is terminated by the addition of 150 µl 167 mM sodium citrate, pH 2.15 containing phosphodiesterase (PDE) SPA beads (0.833 mg/ml). The binding of the radiolabelled product to the bead brings the isotope into close enough proximity to allow radiation from the tritium to excite the scintillant within the bead. Any unbound radiolabel is not close enough to the scintillant to allow this energy transfer, so no signal is generated. Following termination of the reaction, plates are spun at 2500 rpm for 5 min in a Mistral 3000E plate centrifuge (or alternatively allowed to stand for 1 hour). The assay is conducted in 96-well Optiplates (Packard). Plates are counted on a TopCount. (Packard 96 well counter).

Reagents

Mixed E. coli MRE 600 tRNA and ATP were purchased from Boehringer-Mannheim, L-[methyl-³H]methionine and phosphodiesterase scintillation proximity (SPA) beads from Amersham Pharmacia Biotech and other reagents from Sigma.

Results

Examples 5, 8, 13–4, and 28–44, have $IC_{50}$ values against H. influenzae MRS in the range <3 to 2200 nM. All are highly selective with respect to the mammalian enzyme (no inhibition of rat MRS up to 1 µM).

3. Antibacterial Activity

Compounds of the present invention were assayed for antibacterial activity against a range of pathogenic organisms (strains of S aureus, S pneumoniae, E faecalis, H influenzae and M catarrhalis) in a standard MIC assay modified by the inclusion of cyclodextrin, to assist with solubility.

Examples 1–4, 6, 9, 11, 12, 15, 17, 22–30, 32, 34–37, 39–41, and 43–44 had MIC's <1 µg/ml against some strains of the organisms S. aureus, S. pneumoniae, and E. faecalis. Examples 2, 13–24, and 28–44 had MIC's <8 µg/ml against some strains of the organisms M. catarrhalis and H. influenzae.

Compound 3 was tested against a wider range of clinical isolates of S. aureus, Staphylococcus epidermidis, E. faecalis and Enterococcus faecium to determine MIC90 values (the concentration required to inhibit 90% of the organisms). The panels of isolates included a large proportion of organisms resistant to various clinical antibiotics. (See Jarvest, et al., J. Med. Chem., 2002, 45, 1959). Very good activity was seen against all the organisms, with all MIC90 values at ≦1 µg/ml (MIC90's: S. aureus, 1 µg/ml; S. epidermidis, 0.5 µg/ml; E. faecalis, 0.06 µg/ml; and E. faecium 0.03 µg/ml).

The enantiomers of 3 (11(g) and 11(h)) were assayed in the usual way. The (R)-enantiomer was found to be the more active isomer with a lower IC50 value and potent antibacterial activity. The compression of IC50 values <10 nM due to the limit of the enzyme concentration in the assay (3 nM) (see Jarvest, et al., J. Med. Chem., 2002, 45, 1959) makes it hard to calculate the enantiomeric inhibitory ratio. However, the ratio of the antibacterial activity of the two isomers suggests a high degree of enantioselectivity, of the order of at least two orders of magnitude.

In conclusion, the key right hand side pharmacophore for bacterial MRS inhibition has been defined as an NH—C—NH unit in the context of a bicyclic heteroaromatic system. Potent non-quinolone analogues have been obtained with excellent antibacterial activity against staphylococci and enterococci, including antibiotic resistant isolates. In addition, the biologically active configuration of the tetrahydroquinoline series has been identified as possessing (R) stereochemistry.

What is claimed is:

1. A compound of the formula (I):

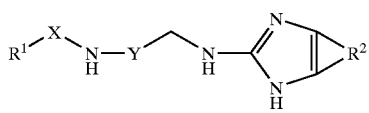

in which:
- R¹ is an optionally substituted aryl or an optionally substituted heteroaryl ring;
- R² is the residue of a 5 or 6-membered heteroaryl ring which is optionally substituted with from 1 to 3 substituents selected from halo, cyano, hydroxy, $(C_{1-6})$alkyl (optionally substituted by halo, hydroxy, amino, mono to perfluoro$(C_{1-3})$alkyl, carboxy or $(C_{1-6})$alkoxycarbonyl), $(C_{3-7})$cycloalkyl, $C_{(1-6)}$alkoxy, amino, mono- or di-$(C_{1-6})$alkylamino, acylamino, carboxy, $(C_{1-6})$alkoxycarbonyl, carboxy$(C_{1-6})$alkyloxy, $(C_{1-6})$alkylthio, $(C_{1-6})$alkylsulphinyl, $(C_{1-6})$alkylsulphonyl, sulphamoyl, mono- and di-$(C_{1-6})$alkylsulphamoyl, carbamoyl, mono- and di-$(C_{1-6})$alkylcarbamoyl, and heterocyclyl;
- X is $CH_2$ or $CHR^3$ in which $R^3$ is $C_{(1-6)}$alkyl or is linked to the ortho position of an aryl or heteroaryl ring of $R^1$ to form a 5 to 7 membered ring optionally including oxygen or nitrogen as a ring atom;
- Y is $C_{(1-3)}$alkylene or $C_{(4-6)}$cycloalkylene;

including tautomeric forms of the imidazole ring; and salts thereof, and excluding 8-[2-(benzylamino)ethylamino]theophylline.

2. A compound according to claim 1, wherein said compound is selected from the group consisting of N-(3,5-dibromobenzyl)-N'-(1H-imidazo[4,5-b]pyridin-2-yl)-propane-1,3-diamine;

N-(4,6-dichloro-1H-indol-2-ylmethyl)-N'-(1H-imidazo[4,5-b]pyridin-2-yl)-propane-1,3-diamine;

N-(6,8-dibromo-1,2,3,4,-tetrahydroquinolin-4-yl)-N'-(1H-imidazo[4,5-b]pyridin-2-yl)-propane-1,3-diamine dihydrochloride;

N-(4,5-dibromothien-2-ylmethyl)-N'-(1H-imidazo[4,5-b]pyridin-2-yl)-propane-1,3-diamine;

N-(3,5-dibromobenzyl)-N'-(1H-imidazo[4,5-c]pyridin-2-yl)-propane-1,3-diamine;

N-(4,6-dichloro-1H-indol-2-ylmethyl)-N'-(1H-imidazo[4,5-b]pyrazin-2-yl)-propane-1,3-diamine dihydrochloride;

N-(4,6-dichloro-1H-indol-2-ylmethyl)-N'-(9H-purin-8-yl)-propane-1,3-diamine dihydrochloride;

N-(4,5-dibromothien-2-ylmethyl)-N'-(9H-purin-8-yl)-propane-1,3-diamine dihydrochloride;

N-(3-bromo-5-methoxy-1H-indol-7-ylmethyl)-N'-(1H-imidazo[4,5-b]pyridin-2-yl)-propane-1,3-diamine;

N-(6-Ethyl-8-iodo-1,2,3,4-tetrahydroquinolin-4-yl)-N'-(1H-imidazo[4,5-b]pyridin-2-yl)-propane-1,3-diamine dihydrochloride;

N-(6,8-dibromo-1,2,3,4-tetrahydroquinolin-4-yl)-N'-(1H-imidazo[4,5-b]pyridin-2-yl)-propane-1,3-diamine dihydrochloride;

N-(3-chloro-5-methoxy-1H-indol-7-ylmethyl)-N'-(1H-imidazo[4,5-b]pyridin-2-yl)-propane-1,3-diamine;

N-(4,5-dibromo-3-methylthiophen-2-ylmethyl)-N'-(1H-imidazo[4,5-c]pyridin-2-yl)propane-1,3-diamine;

N-(4,5-dibromo-3-methylthiophen-2-ylmethyl)-N'-(5H-imidazo[4,5-c]pyridazin-6-yl)propane-1,3-diamine dihydrochloride;

N-(4,5-dibromo-3-methylthiophen-2-ylmethyl)-N'-(1H-imidazo[4,5-b]pyridin-2-yl)propane-1,3-diamine;

N-(4-bromo-3-methyl-5-vinylthiophen-2-ylmethyl)-N'-(5H-imidazo[4,5-c]pyridazin-6-yl)-propane-1,3-diamine;

N-(4-bromo-3-methyl-5-vinylthiophen-2-ylmethyl)-N'-(1H-imidazo[4,5-b]pyridin-2-yl)-propane-1,3-diamine;

N-(4-bromo-3-methyl-5-vinylthiophen-2-ylmethyl)-N'-(1H-imidazo[4,5-c]pyridin-2-yl)-propane-1,3-diamine;

N-(3-bromo-2-ethoxy-5-methylsulfanybenzyl)-N'-(5H-imidazo[4,5-c]pyridazin-6-yl)propane-1,3-diamine dihydrochloride;

N-(6-chloro-8-iodochroman-4-yl)-N'-(5H-imidazo[4,5-c]pyridazin-6-yl)propane-1,3-diamine;

N-(3-chloro-5-methoxy-1H-indol-7-ylmethyl)-N'-(5H-imidazo[4,5-c]pyridazin-6-yl)propane-1,3-diamine dihydrochloride;

N-(4,5-dibromo-3-methylthiophen-2-ylmethyl)-N'-(1H-thieno[3,4-d]imidazol-2-yl)propane-1,3-diamine;

N-(4-bromo-3-methyl-5-vinylthiophen-2-ylmethyl)-N'-(1H-thieno[3,4-d]imidazol-2-yl)propane-1,3-diamine;

N-(3-chloro-5-methoxy-1H-indol-7-ylmethyl)-N'-(1H-thieno[3,4-d]imidazol-2-yl)propane-1,3-diamine;

N-(4-bromo-5-difluoromethyl-3-methylthiophen-2-ylmethyl)-N'-(1H-imidazo[4,5-b]pyridin-2-yl)propane-1,3-diamine dihydrochloride;

N-(4-bromo-5-difluoromethyl-3-methylthiophen-2-ylmethyl)-N'-(5H-imidazo[4,5-c]pyridazin-6-yl)propane-1,3-diamine dihydrochloride;

N-(4-bromo-5-difluoromethyl-3-methylthiophen-2-ylmethyl)-N'-(1H-thieno[3,4-d]imidazol-2-yl)propane-1,3-diamine dihydrochloride;

N-(4-bromo-3-methyl-5-trifluoromethylthiophen-2-ylmethyl)-N'-(5H-imidazo[4,5-c]pyridazin-6-yl)propane-1,3-diamine dihydrochloride;

N-(4-bromo-3-methyl-5-trifluoromethylthiophen-2-ylmethyl)-N'-(1H-thieno[3,4-d]imidazol-2-yl)propane-1,3-diamine dihydrochloride;

N-(4-bromo-3-methyl-5-trifluoromethylthiophen-2-ylmethyl)-N'-(1H-imidazo[4,5-b]pyridin-2-yl)propane-1,3-diamine dihydrochloride;

N-(4-bromo-3-methyl-5-trifluoromethylthiophen-2-ylmethyl)-N'-(1H-imidazo[4,5-c]pyridin-2-yl)propane-1,3-diamine dihydrochloride;

N-(4-bromo-5-(1-fluorovinyl)-3-methylthiophen-2-ylmethyl)-N'-(1H-imidazo[4,5-b]pyridin-2-yl)propane-1,3-diamine hydrochloride;

N-(4-bromo-5-(1-fluorovinyl)-3-methylthiophen-2-ylmethyl)-N'-(1H-imidazo[4,5-c]pyridin-2-yl)propane-1,3-diamine;

N-(4-bromo-5-(1-fluorovinyl)-3-methylthiophen-2-ylmethyl)-N'-(5H-imidazo[4,5-c]pyridazin-6-yl)propane-1,3-diamine;

N-(4-bromo-5-(1-fluorovinyl)-3-methylthiophen-2-ylmethyl)-N'-(1H-thieno[3,4-d]imidazol-2-yl)propane-1,3-diamine;

N-(4-bromo-3-methyl-5-ethynylthiophen-2-ylmethyl)-N'-(5H-imidazo[4,5-c]pyridazin-6-yl)propane-1,3-diamine;

N-(4-bromo-3-methyl-5-ethynylthiophen-2-ylmethyl)-N'-(1H-imidazo[4,5-b]pyridin-2-yl)propane-1,3-diamine;

N-(4-bromo-3-methyl-5-ethynylthiophen-2-ylmethyl)-N'-(1H-imidazo[4,5-c]pyridin-2-yl)propane-1,3-diamine;

N-(4-bromo-3-methyl-5-ethynylthiophen-2-ylmethyl)-N'-(1H-thieno[3,4-d]imidazol-2-yl)propane-1,3-diamine;

N-(4-bromo-5-ethyl-3-(1-propynyl)thiophen-2-ylmethyl)-N'-(5H-imidazo[4,5-c]pyridazin-6-yl)propane-1,3-diamine dihydrochloride;

N-(4-bromo-5-ethyl-3-(1-propynyl)thiophen-2-ylmethyl)-N'-(1H-imidazo[4,5-c]pyridin-2-yl)propane-1,3-diamine;

N-(4-bromo-5-ethyl-3-(1-propynyl)thiophen-2-ylmethyl)-N'-(1H-imidazo[4,5-b]pyridin-2-yl)propane-1,3-diamine;

and N-(4-bromo-5-ethyl-3-(1-propynyl)thiophen-2-ylmethyl)-N'-(1H-thieno[3,4-d]imidazol-2-yl)propane-1,3-diamine.

3. A pharmaceutical composition comprising an antibacterially effective amount of a compound according to claim 1 together with a pharmaceutically acceptable carrier or excipient.

4. A pharmaceutical composition according to claim 3, wherein the compound is selected from the group consisting of N-(3,5-dibromobenzyl)-N'-(1H-imidazo[4,5-b]pyridin-2-yl)-propane-1,3-diamine;

N-(4,6-dichloro-1H-indol-2-ylmethyl)-N'-(1H-imidazo[4,5-b]pyridin-2-yl)-propane-1,3-diamine;

N-(6,8-dibromo-1,2,3,4,-tetrahydroquinolin-4-yl)-N'-(1H-imidazo[4,5-b]pyridin-2-yl)-propane-1,3-diamine dihydrochloride;

N-(4,5-dibromothien-2-ylmethyl)-N'-(1H-imidazo[4,5-b]pyridin-2-yl)-propane-1,3-diamine;

N-(3,5-dibromobenzyl)-N'-(1H-imidazo[4,5-c]pyridin-2-yl)-propane-1,3-diamine;

N-(4,6-dichloro-1H-indol-2-ylmethyl)-N'-(1H-imidazo[4,5-b]pyrazin-2-yl)-propane-1,3-diamine dihydrochloride;

N-(4,6-dichloro-1H-indol-2-ylmethyl)-N'-(9H-purin-8-yl)-propane-1,3-diamine dihydrochloride;

N-(4,5-dibromothien-2-ylmethyl)-N'-(9H-purin-8-yl)-propane-1,3-diamine dihydrochloride;

N-(3-bromo-5-methoxy-1H-indol-7-ylmethyl)-N'-(1H-imidazo[4,5-b]pyridin-2-yl)-propane-1,3-diamine;

N-(6-Ethyl-8-iodo-1,2,3,4-tetrahydroquinolin-4-yl)-N'-(1H-imidazo[4,5-b]pyridin-2-yl)-propane-1,3-diamine dihydrochloride;

N-(6,8-dibromo-1,2,3,4-tetrahydroquinolin-4-yl)-N'-(1H-imidazo[4,5-b]pyridin-2-yl)-propane-1,3-diamine dihydrochloride;

N-(3-chloro-5-methoxy-1H-indol-7-ylmethyl)-N'-(1H-imidazo[4,5-b]pyridin-2-yl)-propane-1,3-diamine;

N-(4,5-dibromo-3-methylthiophen-2-ylmethyl)-N'-(1H-imidazo[4,5-c]pyridin-2-yl)propane-1,3-diamine;

N-(4,5-dibromo-3-methylthiophen-2-ylmethyl)-N'-(5H-imidazo[4,5-c]pyridazin-6-yl)propane-1,3-diamine dihydrochloride;

N-(4,5-dibromo-3-methylthiophen-2-ylmethyl)-N'-(1H-imidazo[4,5-b]pyridin-2-yl)propane-1,3-diamine;

N-(4-bromo-3-methyl-5-vinylthiophen-2-ylmethyl)-N'-(5H-imidazo[4,5-c]pyridazin-6-yl)-propane-1,3-diamine;

N-(4-bromo-3-methyl-5-vinylthiophen-2-ylmethyl)-N'-(1H-imidazo[4,5-b]pyridin-2-yl)-propane-1,3-diamine;

N-(4-bromo-3-methyl-5-vinylthiophen-2-ylmethyl)-N'-(1H-imidazo[4,5-c]pyridin-2-yl)-propane-1,3-diamine;

N-(3-bromo-2-ethoxy-5-methylsulfanybenzyl)-N'-(5H-imidazo[4,5-c]pyridazin-6-yl)propane-1,3-diamine dihydrochloride;

N-(6-chloro-8-iodochroman-4-yl)-N'-(5H-imidazo[4,5-c]pyridazin-6-yl)propane-1,3-diamine;

N-(3-chloro-5-methoxy-1H-indol-7-ylmethyl)-N'-(5H-imidazo[4,5-c]pyridazin-6-yl)propane-1,3-diamine dihydrochloride;

N-(4,5-dibromo-3-methylthiophen-2-ylmethyl)-N'-(1H-thieno[3,4-d]imidazol-2-yl)propane-1,3-diamine;

N-(4-bromo-3-methyl-5-vinylthiophen-2-ylmethyl)-N'-(1H-thieno[3,4-d]imidazol-2-yl)propane-1,3-diamine;

N-(3-chloro-5-methoxy-1H-indol-7-ylmethyl)-N'-(1H-thieno[3,4-d]imidazol-2-yl)propane-1,3-diamine;

N-(4-bromo-5-difluoromethyl-3-methylthiophen-2-ylmethyl)-N'-(1H-imidazo[4,5-b]pyridin-2-yl)propane-1,3-diamine dihydrochloride;

N-(4-bromo-5-difluoromethyl-3-methylthiophen-2-ylmethyl)-N'-(5H-imidazo[4,5-c]pyridazin-6-yl)propane-1,3-diamine dihydrochloride;

N-(4-bromo-5-difluoromethyl-3-methylthiophen-2-ylmethyl)-N'-(1H-thieno[3,4-d]imidazol-2-yl)propane-1,3-diamine dihydrochloride;

N-(4-bromo-3-methyl-5-trifluoromethylthiophen-2-ylmethyl)-N'-(5H-imidazo[4,5-c]pyridazin-6-yl)propane-1,3-diamine;

N-(4-bromo-3-methyl-5-trifluoromethylthiophen-2-ylmethyl)-N'-(1H-thieno[3,4-d]imidazol-2-yl)propane-1,3-diamine dihydrochloride;

N-(4-bromo-3-methyl-5-trifluoromethylthiophen-2-ylmethyl)-N'-(1H-imidazo[4,5-b]pyridin-2-yl)propane-1,3-diamine dihydrochloride;

N-(4-bromo-3-methyl-5-trifluoromethylthiophen-2-ylmethyl)-N'-(1H-imidazo[4,5-c]pyridin-2-yl)propane-1,3-diamine dihydrochloride;

N-(4-bromo-5-(1-fluorovinyl)-3-methylthiophen-2-ylmethyl)-N'-(1H-imidazo[4,5-b]pyridin-2-yl)propane-1,3-diamine hydrochloride;

N-(4-bromo-5-(1-fluorovinyl)-3-methylthiophen-2-ylmethyl)-N'-(1H-imidazo[4,5-c]pyridin-2-yl)propane-1,3-diamine;

N-(4-bromo-5-(1-fluorovinyl)-3-methylthiophen-2-ylmethyl)-N'-(5H-imidazo[4,5-c]pyridazin-6-yl)propane-1,3-diamine;

N-(4-bromo-5-(1-fluorovinyl)-3-methylthiophen-2-ylmethyl)-N'-(1H-thieno[3,4-d]imidazol-2-yl)propane-1,3-diamine;

N-(4-bromo-3-methyl-5-ethynylthiophen-2-ylmethyl)-N'-(5H-imidazo[4,5-c]pyridazin-6-yl)propane-1,3-diamine;

N-(4-bromo-3-methyl-5-ethynylthiophen-2-ylmethyl)-N'-(1H-imidazo[4,5-b]pyridin-2-yl)propane-1,3-diamine;

N-(4-bromo-3-methyl-5-ethynylthiophen-2-ylmethyl)-N'-(1H-imidazo[4,5-c]pyridin-2-yl)propane-1,3-diamine;

N-(4-bromo-3-methyl-5-ethynylthiophen-2-ylmethyl)-N'-(1H-thieno[3,4-d]imidazol-2-yl)propane-1,3-diamine;

N-(4-bromo-5-ethyl-3-(1-propynyl)thiophen-2-ylmethyl)-N'-(5H-imidazo[4,5-c]pyridazin-6-yl)propane-1,3-diamine dihydrochloride;

N-(4-bromo-5-ethyl-3-(1-propynyl)thiophen-2-ylmethyl)-N'-(1H-imidazo[4,5-c]pyridin-2-yl)propane-1,3-diamine;

N-(4-bromo-5-ethyl-3-(1-propynyl)thiophen-2-ylmethyl)-N'-(1H-imidazo[4,5-b]pyridin-2-yl)propane-1,3-diamine;

and N-(4-bromo-5-ethyl-3-(1-propynyl)thiophen-2-ylmethyl)-N'-(1H-thieno[3,4-d]imidazol-2-yl)propane-1,3-diamine.

5. A method of treating a bacterial infection, comprising administering an antibacterially effective amount of a compound according to claim 1 to a patient in need thereof.

6. A method of treating a bacterial infection according to claim 5, wherein the compound is selected from the group consisting of N-(3,5-dibromobenzyl)-N'-(1H-imidazo[4,5-b]pyridin-2-yl)-propane-1,3-diamine;

N-(4,6-dichloro-1H-indol-2-ylmethyl)-N'-(1H-imidazo[4,5-b]pyridin-2-yl)-propane-1,3-diamine;

N-(6,8-dibromo-1,2,3,4,-tetrahydroquinolin-4-yl)-N'-(1H-imidazo[4,5-b]pyridin-2-yl)-propane-1,3-diamine dihydrochloride;

N-(4,5-dibromothien-2-ylmethyl)-N'-(1H-imidazo[4,5-b]pyridin-2-yl)-propane-1,3-diamine;

N-(3,5-dibromobenzyl)-N'-(1H-imidazo[4,5-c]pyridin-2-yl)-propane-1,3-diamine;

N-(4,6-dichloro-1H-indol-2-ylmethyl)-N'-(1H-imidazo[4,5-b]pyrazin-2-yl)-propane-1,3-diamine dihydrochloride;

N-(4,6-dichloro-1H-indol-2-ylmethyl)-N'-(9H-purin-8-yl)-propane-1,3-diamine dihydrochloride;

N-(4,5-dibromothien-2-ylmethyl)-N'-(9H-purin-8-yl)-propane-1,3-diamine dihydrochloride;

N-(3-bromo-5-methoxy-1H-indol-7-ylmethyl)-N'-(1H-imidazo[4,5-b]pyridin-2-yl)-propane-1,3-diamine;

N-(6-Ethyl-8-iodo-1,2,3,4-tetrahydroquinolin-4-yl)-N'-(1H-imidazo[4,5-b]pyridin-2-yl)-propane-1,3-diamine dihydrochloride;

N-(6,8-dibromo-1,2,3,4-tetrahydroquinolin-4-yl)-N'-(1H-imidazo[4,5-b]pyridin-2-yl)-propane-1,3-diamine dihydrochloride;

N-(3-chloro-5-methoxy-1H-indol-7-ylmethyl)-N'-(1H-imidazo[4,5-b]pyridin-2-yl)-propane-1,3-diamine;

N-(4,5-dibromo-3-methylthiophen-2-ylmethyl)-N'-(1H-imidazo[4,5-c]pyridin-2-yl)propane-1,3-diamine;

N-(4,5-dibromo-3-methylthiophen-2-ylmethyl)-N'-(5H-imidazo[4,5-c]pyridazin-6-yl)propane-1,3-diamine dihydrochloride;

N-(4,5-dibromo-3-methylthiophen-2-ylmethyl)-N'-(1H-imidazo[4,5-b]pyridin-2-yl)propane-1,3-diamine;

N-(4-bromo-3-methyl-5-vinylthiophen-2-ylmethyl)-N'-(5H-imidazo[4,5-c]pyridazin-6-yl)-propane-1,3-diamine;

N-(4-bromo-3-methyl-5-vinylthiophen-2-ylmethyl)-N'-(1H-imidazo[4,5-b]pyridin-2-yl)-propane-1,3-diamine;

N-(4-bromo-3-methyl-5-vinylthiophen-2-ylmethyl)-N'-(1H-imidazo[4,5-c]pyridin-2-yl)-propane-1,3-diamine;

N-(3-bromo-2-ethoxy-5-methylsulfanybenzyl)-N'-(5H-imidazo[4,5-c]pyridazin-6-yl)propane-1,3-diamine dihydrochloride;

N-(6-chloro-8-iodochroman-4-yl)-N'-(5H-imidazo[4,5-c]pyridazin-6-yl)propane-1,3-diamine;

N-(3-chloro-5-methoxy-1H-indol-7-ylmethyl)-N'-(5H-imidazo[4,5-c]pyridazin-6-yl)propane-1,3-diamine dihydrochloride;

N-(4,5-dibromo-3-methylthiophen-2-ylmethyl)-N'-(1H-thieno[3,4-d]imidazol-2-yl)propane-1,3-diamine;

N-(4-bromo-3-methyl-5-vinylthiophen-2-ylmethyl)-N'-(1H-thieno[3,4-d]imidazol-2-yl)propane-1,3-diamine;

N-(3-chloro-5-methoxy-1H-indol-7-ylmethyl)-N'-(1H-thieno[3,4-d]imidazol-2-yl)propane-1,3-diamine;

N-(4-bromo-5-difluoromethyl-3-methylthiophen-2-ylmethyl)-N'-(1H-imidazo[4,5-b]pyridin-2-yl)propane-1,3-diamine dihydrochloride;

N-(4-bromo-5-difluoromethyl-3-methylthiophen-2-ylmethyl)-N'-(5H-imidazo[4,5-c]pyridazin-6-yl)propane-1,3-diamine dihydrochloride;

N-(4-bromo-5-difluoromethyl-3-methylthiophen-2-ylmethyl)-N'-(1H-thieno[3,4-d]imidazol-2-yl)propane-1,3-diamine dihydrochloride;

N-(4-bromo-3-methyl-5-trifluoromethylthiophen-2-ylmethyl)-N'-(5H-imidazo[4,5-c]pyridazin-6-yl)propane-1,3-diamine dihydrochloride;

N-(4-bromo-3-methyl-5-trifluoromethylthiophen-2-ylmethyl)-N'-(1H-thieno[3,4-d]imidazol-2-yl)propane-1,3-diamine dihydrochloride;

N-(4-bromo-3-methyl-5-trifluoromethylthiophen-2-ylmethyl)-N'-(1H-imidazo[4,5-b]pyridin-2-yl)propane-1,3-diamine dihydrochloride;

N-(4-bromo-3-methyl-5-trifluoromethylthiophen-2-ylmethyl)-N'-(1H-imidazo[4,5-c]pyridin-2-yl)propane-1,3-diamine dihydrochloride;

N-(4-bromo-5-(1-fluorovinyl)-3-methylthiophen-2-ylmethyl)-N'-(1H-imidazo[4,5-b]pyridin-2-yl)propane-1,3-diamine hydrochloride;

N-(4-bromo-5-(1-fluorovinyl)-3-methylthiophen-2-ylmethyl)-N'-(1H-imidazo[4,5-c]pyridin-2-yl)propane-1,3-diamine;

N-(4-bromo-5-(1-fluorovinyl)-3-methylthiophen-2-ylmethyl)-N'-(5H-imidazo[4,5-c]pyridazin-6-yl)propane-1,3-diamine;

N-(4-bromo-5-(1-fluorovinyl)-3-methylthiophen-2-ylmethyl)-N'-(1H-thieno[3,4-d]imidazol-2-yl)propane-1,3-diamine;

N-(4-bromo-3-methyl-5-ethynylthiophen-2-ylmethyl)-N'-(5H-imidazo[4,5-c]pyridazin-6-yl)propane-1,3-diamine;

N-(4-bromo-3-methyl-5-ethynylthiophen-2-ylmethyl)-N'-(1H-imidazo[4,5-b]pyridin-2-yl)propane-1,3-diamine;

N-(4-bromo-3-methyl-5-ethynylthiophen-2-ylmethyl)-N'-(1H-imidazo[4,5-c]pyridin-2-yl)propane-1,3-diamine;

N-(4-bromo-3-methyl-5-ethynylthiophen-2-ylmethyl)-N'-(1H-thieno[3,4-d]imidazol-2-yl)propane-1,3-diamine;

N-(4-bromo-5-ethyl-3-(1-propynyl)thiophen-2-ylmethyl)-N'-(5H-imidazo[4,5-c]pyridazin-6-yl)propane-1,3-diamine dihydrochloride;

N-(4-bromo-5-ethyl-3-(1-propynyl)thiophen-2-ylmethyl)-N'-(1H-imidazo[4,5-c]pyridin-2-yl)propane-1,3-diamine;

N-(4-bromo-5-ethyl-3-(1-propynyl)thiophen-2-ylmethyl)-N'-(1H-imidazo[4,5-b]pyridin-2-yl)propane-1,3-diamine;

and N-(4-bromo-5-ethyl-3-(1-propynyl)thiophen-2-ylmethyl)-N'-(1H-thieno[3,4-d]imidazol-2-yl)propane-1,3-diamine.

7. A process for preparing a compound of formula (I) of claim 1 which process comprises (i) reacting an imidazole compound of formula (II):

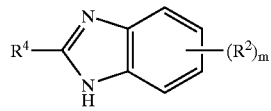 (II)

in which $R^2$ is as hereinbefore defined; and $R^4$ is a leaving group such as halo, for instance chloro or $C_{(1-6)}$alkylthio;

with an amine of the formula (III):

 $R^1XNHYCH_2NH_2$ (III)

in which $R^1$, X and Y are as hereinbefore defined;
under nucleophilic displacement conditions; or (ii) reacting a compound of formula (IV):

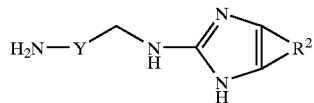 (IV)

in which $R^2$ and Y are as hereinbefore defined;

with either:

(a) for a compound of formula (I) in which X is $CH_2$, an aldehyde of formula (V):

 $R^1CHO$ (V)

in which $R^1$ is as hereinbefore defined;

under reductive alkylation conditions;

(b) for a compound of formula (I) in which X is $CHR^3$, a ketone of formula (VI):

 $R^1R^3CO$ (VI)

in which $R^1$ and $R^3$ are as hereinbefore defined;

under reductive alkylation conditions;

(c) for preparing a compound of formula (I) in which Y is $C_{(1-3)}$alkylene which process comprises reacting a compound of formula (VII):

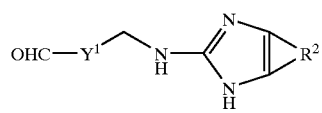 (VII)

in which $R^2$ is as hereinbefore defined, and $Y^1$ is $C_{(0-2)}$alkylene;

with an amine of formula (VIII):

 $R^1XNH_2$ (VIII)

in which $R^1$ and X are as hereinbefore defined;
under reductive alkylation conditions.

* * * * *